US006596529B1

(12) United States Patent
Wertz et al.

(10) Patent No.: US 6,596,529 B1
(45) Date of Patent: *Jul. 22, 2003

(54) MANIPULATION OF NEGATIVE STRANDED RNA VIRUSES BY REARRANGEMENT OF THEIR GENES AND USES THEREOF

(75) Inventors: Gail W. Wertz, Birmingham, AL (US); L. Andrew Ball, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,288

(22) Filed: Jun. 23, 2000

Related U.S. Application Data

(63) Continuation-in-part of application No. 09/071,606, filed on May 1, 1998, now Pat. No. 6,136,585.
(60) Provisional application No. 60/045,471, filed on May 2, 1997, now abandoned.

(51) Int. Cl.[7] ................................................. C12N 7/04
(52) U.S. Cl. ................................... 435/236; 424/224.1
(58) Field of Search ......................... 435/236; 424/224.1

(56) References Cited

U.S. PATENT DOCUMENTS 6,136,585 A * 10/2000 Ball et al. ................... 435/236

* cited by examiner

Primary Examiner—Donna C. Wortman
(74) Attorney, Agent, or Firm—Benjamin Aaron Adler

(57) ABSTRACT

The present invention provides a method of increasing expression of a promoter distal gene in a virus of the order Mononegavirales, and a recombinant virus constructed by such method. Also provided is a method of attenuating a virus of the order Mononegavirales, and of constructing an attenuated virus useful for a vaccine.

3 Claims, 28 Drawing Sheets

| | | |
|---|---|---|
| R4 (Wild-type) | 3'- leader - N - P - M - G - L - trailer - 5' | |
| R1 | 3'- leader - N - G - M - P - L - trailer - 5' | |
| R2 | 3'- leader - N - M - G - P - L - trailer - 5' | |
| R3 | 3'- leader - N - P - G - M - L - trailer - 5' | |
| R5 | 3'- leader - N - G - P - M - L - trailer - 5' | |
| R6 | 3'- leader - N - M - P - G - L - trailer - 5' | |
| R7 | 3'- leader - P - N - M - G - L - trailer - 5' | |
| R8 | 3'- leader - P - M - N - G - L - trailer - 5' | |
| R9 | 3'- leader - P - M - G - N - L - trailer - 5' | |
| R10 | 3'- leader - G - N - P - M - L - trailer - 5' | |
| R11 | 3'- leader - G - P - M - N - L - trailer - 5' | |

BspM1 5′ ...ACCTGCNNNN 3′
3′ TGGACGNNNNNNNN 5′ (SEQ ID No. 4)

Bsa1 5′...GGTCTCN 3′
3′ .CCAGAGNNNNN 5′ (SEQ ID No. 5)

Hind3 BspM1
Upstream PCR primer 5′ GGGAAGCTTACCTGCACTAACAGNNATNNN 3′ (SEQ ID No. 6)

VSV IC junction
5′...TATGAAAAAAACTAACAGNNATNNN...3′ (SEQ ID No. 7)
3′...ATACTTTTTTTGATTGTCNNTANNN...5′

Downstream PCR primer 3′ CTTTTTTTGATTGTCNNTACGTCCAGGGCCCACG 5′
BspM1 Ava1 (SEQ ID No. 8)

GCACCCGGGACCTGCATATCTGTTACTTTTTTTC P Downstream (SEQ ID No. 9)
GCACCCGGGACCTGCATCTCTGTTAGTTTTTTTC M Downstream (SEQ ID No. 10)
GCACCCGGGACCTGCATTGCTGTTAGTTTTTTTC G Downstream (SEQ ID No. 11)

GCACCCGGGACCTGCATATCTGTTACTTTTTTTC Consensus downstream (SEQ ID No. 12)
CG
T

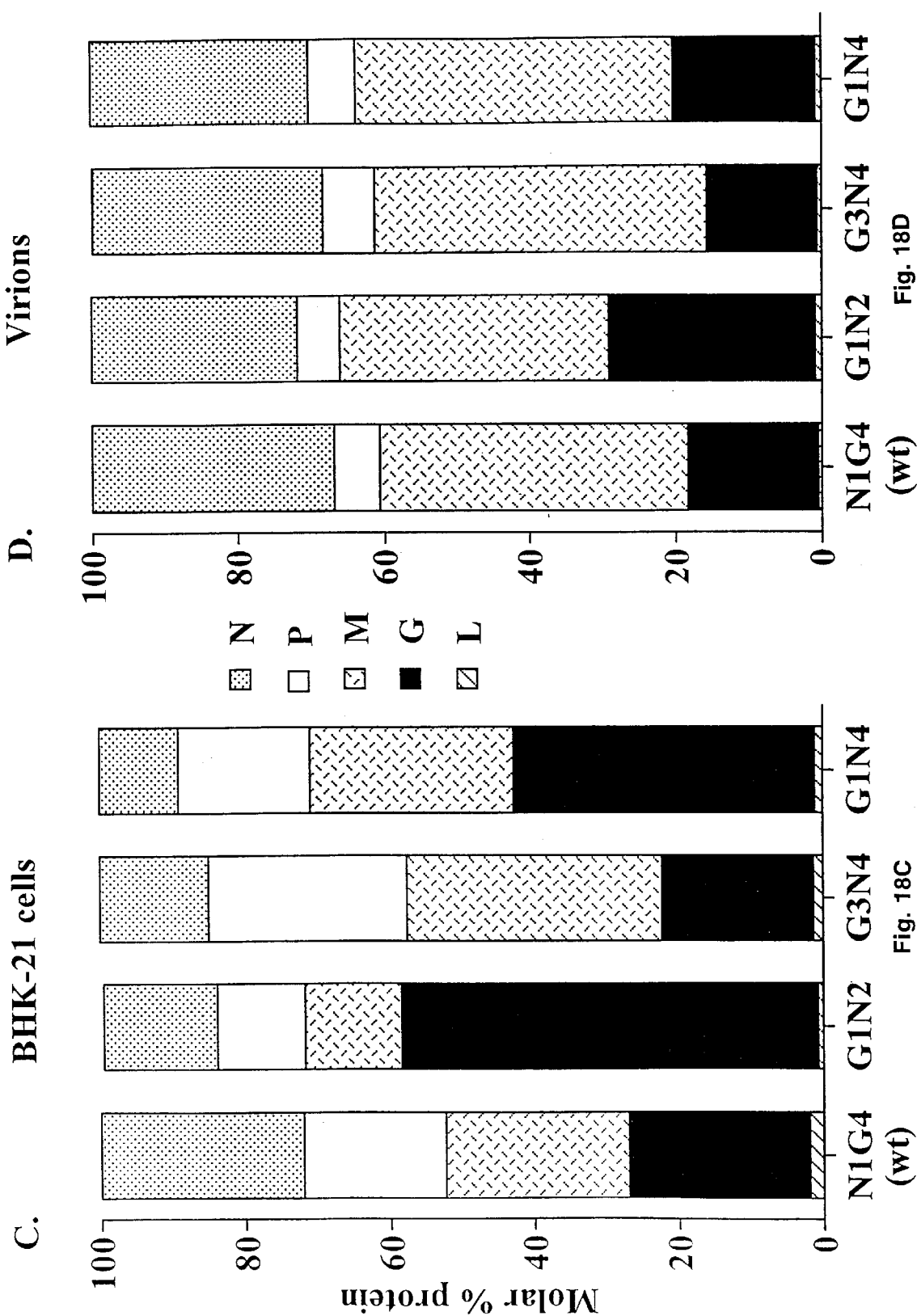

MANIPULATION OF NEGATIVE STRANDED RNA VIRUSES BY REARRANGEMENT OF THEIR GENES AND USES THEREOF

CROSS-REFERENCE TO RELATED APPLICATION

This application is a continuation-in-part and claims the benefit of priority under 35 USC §120 of U.S. patent application Ser. No. 09/071,606, filed May 1, 1998, now U.S. Pat. No. 6,136,585, which claims benefit of priority under 35 U.S.C. 119(e) of U.S. provisional application Ser. No. 60/045,471, filed May 2, 1997, now abandoned.

BACKGROUND OF THE INVENTION

1. Field of the Invention

The present invention relates generally to the fields of molecular virology and vaccinology. More specifically, the present invention relates to the attenuation of negative stranded RNA viruses by rearrangement of their genes and uses thereof.

2. Description of the Related Art

The order Mononegavirales is composed of four families, the Rhabdoviridae, the Paramyxoviridae, the Filoviridae and the Bornaviridae. The viruses in these families contain a single strand of non-segmented negative-sense RNA and are responsible for a wide range of significant diseases in fish, plants, and animals (Wagner, 1996). The expression of the genes encoded by these viruses is controlled at the level of transcription by the order of the genes on the genome relative to the single 3' promoter. Gene order throughout the Mononegavirales is highly conserved: genes encoding products required in stoichiometric amounts for replication are always at or near the 3' end of the genome while those whose products are needed in catalytic amounts are more promoter distal (Pringle and Easton, 1997).

Vesicular stomatitis virus (VSV) is the prototypic virus of the Rhabdoviridae. Its 11 kilobase genome has 5 genes which encode the 5 structural proteins of the virus; the nucleocapsid protein, N, which is required in stoichiometric amounts for encapsidation of the replicated RNA; the phosphoprotein, P, which is a cofactor of the RNA-dependent RNA polymerase, L; the matrix protein, M; and the attachment glycoprotein, G. The order of genes in the genome is 3'-N-P-M-G-L-5' and previous studies have shown that expression is obligatorily sequential from a single 3' promoter (Ball and White, 1976). Due to attenuation at each gene junction the 3'-most genes are transcribed more abundantly than those that are more promoter distal (Iverson and Rose, 1981).

In nature, VSV infects a wide range of animals of which horses, cattle, and domestic swine are the most economically important. Infection results in the appearance of lesions around the mouth, hooves, and udder teats and while seldom fatal it leads to a loss in meat and milk production along with the expense of quarantine and vaccination. There are two main VSV serotypes, Indiana (Ind) and New Jersey (NJ) and while these viruses are endemic in Central and South American countries, outbreaks do occur within the United States. A recent outbreak in the U.S. occurred in 1997 in horses, and was of the Ind serotype while previous cases identified in 1995 and 1982–1983 were of the NJ serotype. The ease with which these viruses are transmitted, and the similarity of their symptoms to those caused by foot-and-mouth disease virus in cattle and domestic swine, makes VSV a pathogen of concern to the agriculture industry.

Live attenuated viruses capable of replicating to generate protective humoral as well as cell mediated immune responses without producing disease manifestations have proven effective vaccines against viruses such as smallpox, yellow fever and poliomyelitis. The strategy for attenuation, however, has been empirical in most cases and not reproducible for general use. An additional consideration in the case of RNA viruses is that the high error rate of RNA dependent RNA polymerases, their lack of proof reading and the quasi-species nature of RNA virus populations (Domingo et al, 1996), make the use of live attenuated viruses for this large group of medically significant pathogens problematic. This is especially true if the vaccine virus is based on a limited number of single base changes as reversion to virulence is a potential problem. For example, only a few back mutations can restore virulence to the Sabin poliovirus type 3 vaccine strain (Wimmer et al., 1993).

The non-segmented negative strand RNA viruses of the family Mononegavirales possess an elegantly simple means of controlling the expression of their genes. The linear, single-stranded RNA genomes of this family encode five to ten genes, the order of which is highly conserved among all members. The prototype virus of this family is the Rhabdovirus, vesicular stomatitis virus (VSV). Transcription of the viral genome is carried out by the virus-encoded RNA dependent RNA polymerase. There is a single entry site on the linear genome for the RNA polymerase, yet the mRNAs of the virus are not produced in equimolar amounts.

Available evidence indicates that the linear order of the genes on the genome controls the levels of expression of individual genes. Transcription initiates at the single polymerase entry site at the 3' terminus of the genome and is obligatorily processive (Ball and White, 1976). The level of expression of the individual genes a s monocistronic mRNAs is controlled by the dissociation, approximately 30% of the time, of the polymerase at each intergenic junction, as it traverses the genome in the 3' to 5' direction (Iverson and Rose, 1981). This mechanism of transcription results in sequentially decreasing amounts of the transcripts of each gene as a function of the distance of the gene from the 3' terminus of the genome. Correspondingly, gene products needed in stoichiometric amounts to support replication, such as the nucleocapsid (N) protein, are encoded at or near the 3' terminus in all cases and expressed in the highest molar amounts (Villarreal et al., 1976, Ball and White, 1976). Gene products needed in enzymatic amounts, such as the RNA polymerase are encoded most distal from the 3' end. In all of the Mononegavirales, the polymerase gene is the 5'-most gene, and it is expressed in the lowest amount. Precise molar ratios of the proteins are required for optimal replication. For successful replication, proteins must be expressed in molar ratios that approximate those expressed normally from the genome (Pattnaik and Wertz, 1990).

Viruses of the family Mononegavirales do not undergo homologous genetic recombination (Pringle, 1987). Thus, other than defective interfering particles, which lack portions of the genome, variants of these viruses having the entire complement of genes in a rearranged format have not been observed in nature.

The prior art is deficient in the lack of effective means of increasing expression of a promoter distal gene in a virus of the order Mononegavirales and uses of such viruses. The present invention fulfills this long-standing need and desire in the art.

SUMMARY OF THE INVENTION

The non-segmented negative-strand RNA viruses (order Mononegavirales) comprise several important human pathogens. The order of their genes, which is highly conserved, is the major determinant of the relative levels of gene expression, since genes that are close to the single promoter site on the viral genome are transcribed at higher levels than those that occupy more distal positions. An infectious cDNA clone of the prototypic vesicular stomatitis virus (VSV) was manipulated to rearrange the order of four of the five viral genes, while leaving all other aspects of the viral nucleotide sequence unaltered. In one set of cDNA clones, the middle three genes (which encode the phosphoprotein P, the matrix protein M, and the glycoprotein G) were rearranged into all six possible orders. In another set, the gene for the nucleocapsid protein N was moved away from its wild-type promoter-proximal position and placed second, third or fourth. In a final rearrangement, the G protein gene, which encodes the major surface antigen and the target for neutralizing antibodies, was put next to the promoter, in the position for maximum expression. Infectious viruses were recovered from each of these rearranged cDNAs and examined for their levels of gene expression and growth potential in cell culture, and their immunogenicity and virulence in mice. Rearrangement changed the expression levels of the encoded proteins and attenuated the viruses to different extents both in cultured cells and in mice. Increasing the expression of the G protein enhanced and accelerated the immune response in inoculated mice. Since the Mononegavirales do not undergo homologous recombination, gene rearrangement should be irreversible and thus provides a rational method for developing securely attenuated live vaccines against this type of virus.

In one embodiment of the present invention, there is provided a method of increasing expression of a promoter distal gene in a virus of the order Mononegavirales, comprising the step of rearranging gene order of the virus by moving the promoter distal gene toward a wild-type 3' promoter proximal position site.

In another embodiment of the present invention, there is provided a recombinant virus of the order Mononegavirales having a rearranged genome, wherein the genome is rearranged by moving a promoter distal gene of the virus toward a wild type 3' promoter proximal position site. Such recombinant virus can be used for accelerating and enhancing a protective immune response.

In still another embodiment of the present invention, there is provided a method of attenuating a virus of the order Mononegavirales by rearranging gene order of the virus by moving a gene away from its wild type position, or by rearranging gene order of the virus by moving an essential limiting factor gene away from its wild type 3' promoter proximal position site.

In yet another embodiment of the present invention, there is provided a method of constructing an attenuated virus useful for a vaccine, comprising the steps of: rearranging the gene order of the virus by moving a gene away from its wild-type 3' promoter proximal position site, wherein the gene is an essential limiting factor for genome replication; and placing a gene coding for an immune response inducing antigen in the position closest to the 3' end of the gene order of the virus.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the gene orders of the rearranged VSV genomes.

Figure 2:
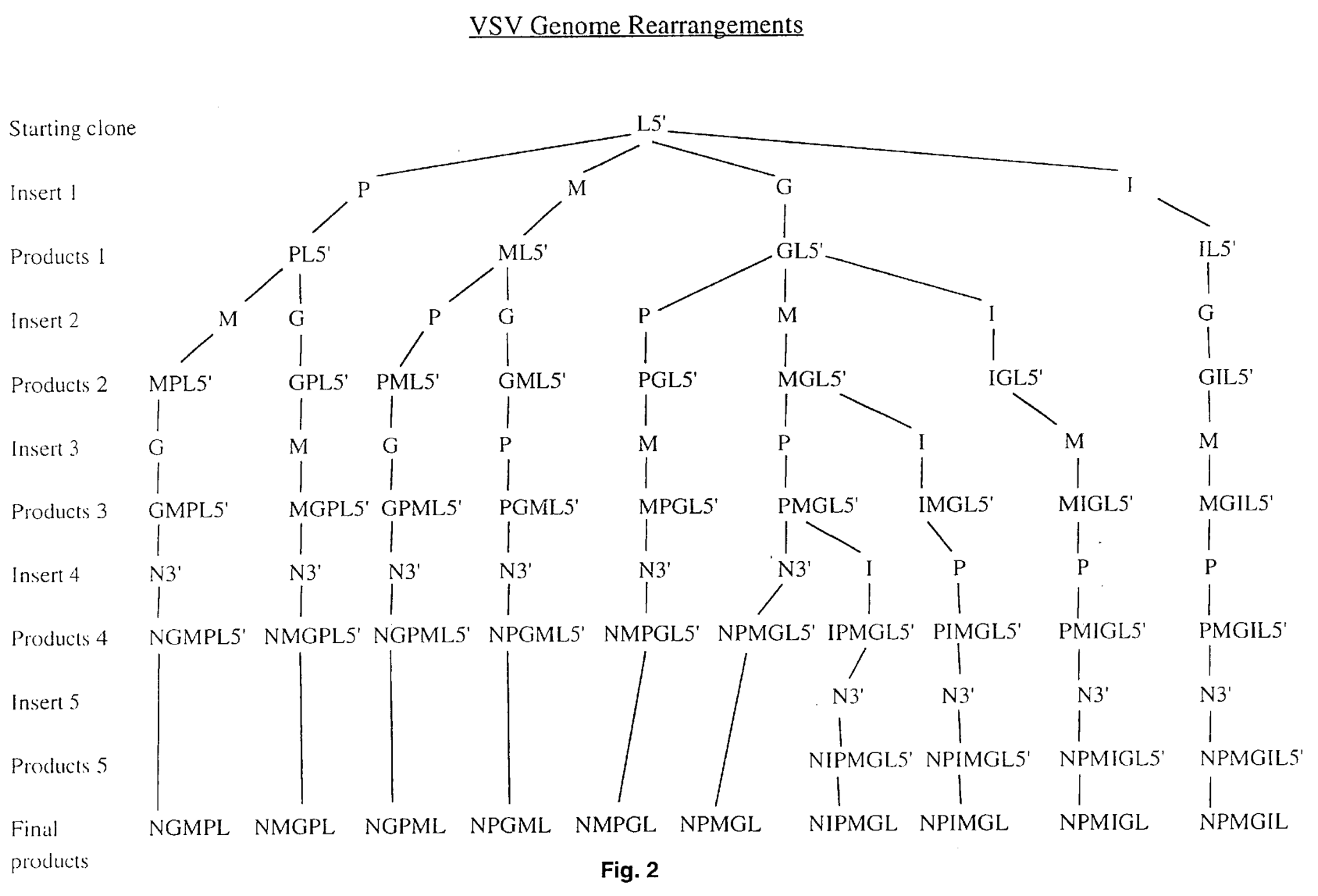

FIG. 2 shows the stepwise procedure for generation of rearranged VSV genomic cDNAs.

FIG. 3A shows the cleavage specificity of restriction enzymes used to generate cDNA modules for gene order rearrangement. Using PCR, either a BspMI or BsaI site is positioned at each end of the P, M and G genes of VSV, and at the 3' end of the N gene and the 5' end of the L gene, such that the sticky ends correspond to 4 of the conserved nucleotides at the intercistronic junctions.

FIG. 18 shows synthesis of viral proteins in BHK-21 cells infected with the variant viruses.

DETAILED DESCRIPTION OF THE INVENTION

Figure 3B:
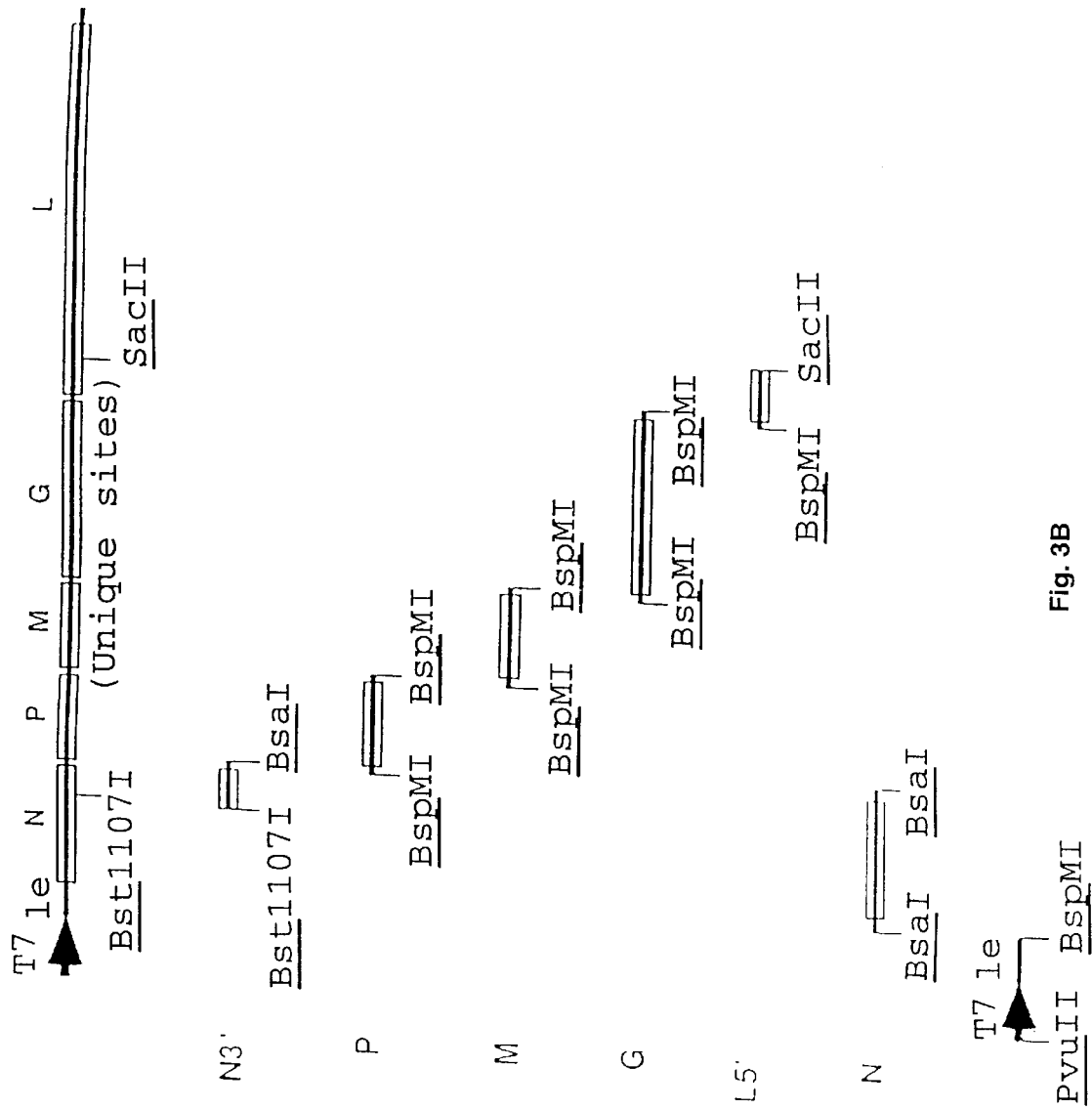
FIG. 3B shows fragments of VSV genome cloned for gene order rearrangement.
Figure 4:
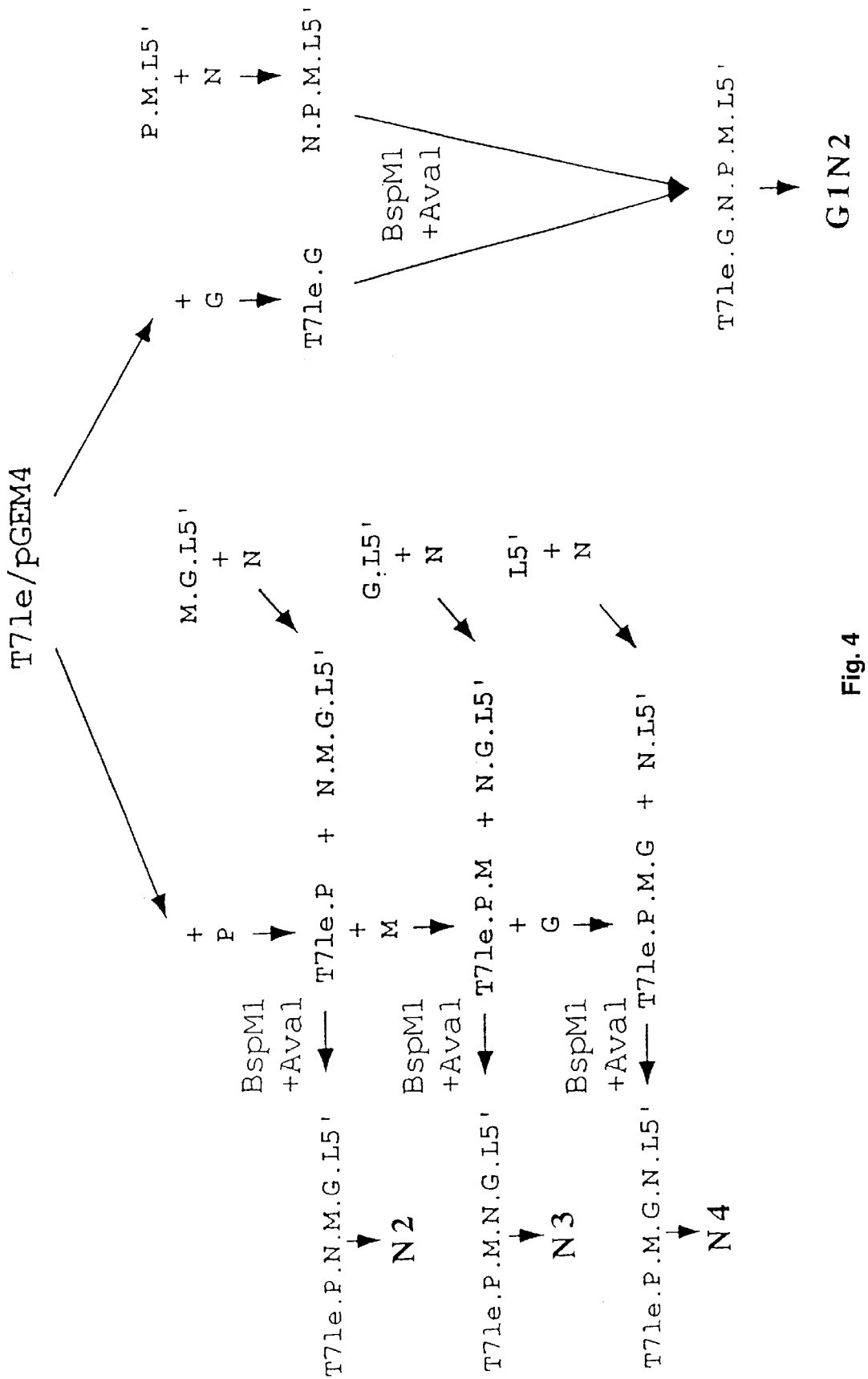
FIG. 4 shows the strategy for construction of rearranged genomes N2, N3, N4 and G1N2.

The present invention illustrates that introduction of specific changes into the genome of a negative strand RNA virus allowed translocation of the gene for the nucleocapsid (N) protein to successive positions on the genome and demonstrated directly that the position of a gene relative to the promoter determined the level of expression. Levels of N protein synthesis control the level of RNA replication. Consistent with this, the present invention demonstrates that as the level of N mRNA and protein synthesis in cells infected with viruses N2, N3 and N4 was reduced, the level of genomic RNA replication was also reduced. Correspondingly, the production of infectious virus in cell culture was reduced in increments up to four orders of magnitude with virus N4. Finally, concomitant with reduced replication potential, the lethality of viruses N2, N3, and N4 for mice following IN inoculation was reduced by approximately one, two or three orders of magnitude, respectively, compared to the wild-type virus.

These data demonstrate that translocating a single gene essential for replication to successive positions down the viral genome lowered the growth potential in cell culture and the lethality of the viruses for mice in a stepwise manner. However, the ability of the viruses to elicit a protective immune response in mice was not altered in correspondence with the reduction in virulence. Therefore, since the viruses all contained the wild-type complement of genes and all were competent to replicate, albeit at reduced levels, the level of replication was sufficient to induce a protective host response. Thus, for some rearranged viruses, the protective dose and the lethal dose were 1,000 fold different, in contrast to the situation with wild-type virus where the lethal dose and protective dose overlap. Taken together, these data suggest a means of attenuating non-segmented negative strand RNA viruses in a predictable, incremental manner that would allow one to determine an optimal level of attenuation to avoid disease production without loss of replication potential to induce a sufficient immune response.

Since the Mononegavirales have not been observed to undergo homologous recombination, gene rearrangement is predicted to be irreversible, and therefore, the present invention provides a rational, alternative method for developing stably attenuated live vaccines against the non-segmented negative strand RNA viruses. Furthermore, based on the close similarity of genome organization and control of gene expression, this approach to generating attenuated viruses should be applicable to the entire family of Mononegavirales, which includes the Rhabdoviridae, such as rabies, the Paramyxoviridae, such as measles, mumps, respiratory syncytial virus, and parainfluenza viruses I–IV, and the Filoviridae such as Ebola and Marburg viruses. These represent some of the most problematic viral pathogens extent.

In one embodiment of the present invention, there is provided a method of increasing expression of a promoter distal gene in a virus of the order Mononegavirales, comprising the step of rearranging gene order of the virus by moving the promoter distal gene toward a wild-type 3' promoter proximal position site. Preferably, the distal gene encodes a surface glycoprotein. For vesicular stomatitis virus, one distal gene that encodes a surface glycoprotein is the gene for the attachment glycoprotein G. For respiratory syncytial virus, one distal gene that encodes a surface glycoprotein is referred to as the attachment glycoprotein (G) gene; another distal gene that encodes a surface glycoprotein is the respiratory syncytial virus fusion (F) protein gene. For the measles virus, the distal gene that encodes a surface glycoprotein is referred to as the H (hemagglutinin) gene. For the mumps and parainfluenza viruses, the distal gene that encodes a surface glycoprotein is referred to as the HN (hemagglutinin/neuraminidase) gene. A person having ordinary skill in this art would readily recognize, for each specific virus of the order Mononegavirales, which distal gene that encodes a surface glycoprotein would be manipulated in order to perform the methods of the present invention.

In another embodiment of the present invention, there is provided a recombinant virus of the order Mononegavirales having a rearranged genome, wherein the genome is rearranged by moving a promoter distal gene of the virus toward a wild type 3' promoter proximal position site. Such recombinant virus can be used for accelerating and enhancing a protective immune response.

In still another embodiment of the present invention, there is provided a method of attenuating a virus of the order Mononegavirales by rearranging gene order of the virus by moving a gene away from its wild type position, or by rearranging gene order of the virus by moving an essential limiting factor gene away from its wild type 3' promoter proximal position site. Preferably, the gene is placed in the next to last position in the gene order of the virus. Furthermore, it is preferable that the gene which is an essential limiting factor for genome replication is the nucleocapsid (N) gene. Representative examples of viruses of the order Mononegavirales are a Rhabdovirus, such as rabies virus or vesicular stomatitis virus, a Paramyxovirus, such as measles, mumps, parainfluenza virus or respiratory syncytial virus (human and bovine), or a Filovirus, such as Ebola virus or Marburg virus. The present invention also includes a virus attenuated according to this method.

In yet another embodiment of the present invention, there is provided a method of constructing an attenuated virus useful for a vaccine, comprising the steps of rearranging gene order of the virus by moving a gene away from its wild-type 3' promoter proximal position site, wherein the gene is an essential limiting factor for genome replication; and placing a gene coding for an immune response inducing antigen in the position closest to the 3' end of the gene order of the virus. Preferably, the essential limiting factor gene is the nucleocapsid (N) gene and the gene is placed in the next to last position in the gene order of the virus. Still preferably, the gene coding for an immune response inducing antigen may be the attachment glycoprotein (G) gene, a fusion gene or the hemagglutinin/neuraminidase gene. A person having ordinary skill in this art would be able to readily substitute suitable immune response-inducing antigens. The present invention also includes a virus attenuated according to this method.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the non-transcribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA molecule. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Delgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence. "Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA or RNA molecule or gene of the present invention can be used to transform a host using any of the techniques commonly known to those of ordinary skill in the art. One preferred embodiment is the use of a vectors containing coding sequences for the RNA molecules or cDNA molecules of the present invention for purposes of transformation. Prokaryotic hosts may include *E. coli, S. typhimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the gene in transgenic systems, in accordance with conventional Southern hybridization techniques known to those of ordinary skill in the art. Both the Northern blot and Southern blot use a hybridization probe, e.g. radiolabeled cDNA, either containing the full-length, single stranded DNA or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art. Alternatively, the label may be incorporated directly into the RNA or protein molecule by many different methods known to those of skill in this art.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "attenuation" is defined as either a genetic mechanism involving premature termination of transcription used to regulate expression of a gene, or immunologically, the process whereby a pathogenic microorganism loses its virulence.

As used herein, the term "lethal dose" is defined as the amount of virus inoculum required to confer lethality on the host.

As used herein, the term "protective dose" is defined as the amount of virus inoculum that produces a sufficient immune response towards the virus without resulting in lethality.

As used herein, the term "rearrangement" is defined as the reordering of the genes within the viral genome, such that the gene and the intergenic regions remain wild-type and only the order with respect to the 3' terminus is altered.

As used herein, the term "negative strand RNA virus" is defined as a classification of RNA viruses in which the genome comprises the negative strand of an RNA molecule.

The present invention also demonstrates that it is possible to increase the expression of a promoter distal gene, e.g., the G gene, which encodes the attachment glycoprotein, by moving it to a promoter proximal site. To show that an increase in the production of the G protein during infection could elicit a greater protective immune response, changes were engineered into an infectious cDNA clone of the VSV genome and two novel viruses were recovered in which the glycoprotein gene was moved from its normal fourth position to the first position in the gene order. One virus had the gene order 3'-G-N-P-M-L-5' (G1N2) and the second 3'-G-P-M-N-L-5' (G1N4). The in vitro and in vivo characteristics of these viruses were assessed and compared to those of viruses having the gene orders 3'-P-M-G-N-L-5' (G3N4) and 3'-N-P-M-G-L-5' (N1G4), the latter being the wild-type gene order. Differences were observed in the replication of these viruses in cell culture, lethality in mice, kinetics and levels of antibody production, and their ability to protect against challenge with a lethal dose of VSV.

The following examples are given for the purpose of illustrating various embodiments of the invention and are not meant to limit the present invention in any fashion.

Example 1

Viruses and Cells

The San Juan isolate of the Indiana serotype of VSV provided the original template for most of the cDNA clones used herein. However, the gene encoding the G protein was originally derived from the Orsay isolate of VSV Indiana (Whelan et al., 1995). Baby hamster kidney (BHK-21) cells were used to recover viruses from cDNAs and for single step growth experiments and radioisotopic labeling of RNAs and proteins. African green monkey kidney (BSC-1 and BSC-40) cells were used for plaque assays.

Example 2

Plasmid Construction and Recovery of Infectious Viruses

Each of the five genes of VSV is flanked by a common sequence of eighteen nucleotides. Thus, it was possible to construct individual molecular clones from which DNA fragments precisely encompassing each gene could be released by digestion with an appropriate restriction endonuclease. Restriction endonucleases that cut at site remote from their recognition sequences were used to create gene segments having cohesive ends that corresponded to the same four nucleotides (ACAG) of the conserved intercistronic regions. In this way, the DNA segments that encompassed each of the five genes could be reassembled in any desired order to create a family of DNA plasmids whose nucleotide sequences corresponded precisely to that of wild-type VSV, except for the fact that their genes were rearranged. A diagram of the steps involved in the construction of the rearranged virus genomes N1 (wt), GMP, MGP, PGM, GPM, MPG, N2, N3, N4, G1N2 and G1N4 is shown in FIGS. 2, 3A, 3B, and 4.

Infectious viruses were recovered from these DNA plasmids by methods described (Whelan et al., 1995). Briefly, BHK cells were infected with the vaccinia virus recombinant that expresses T7 RNA polymerase, VTF7-3, (Fuerst et al., 1986) and cotransfected with one of the rearranged cDNA plasmids and the three support plasmids that express the N, P and L proteins required for RNA encapsidation and replication. Infectious viruses were recovered from the supernatant of transfected cells, amplified by low-multiplicity passage on BHK-21 cells, and filtered through 0.2 mm filters to remove contaminating VTF7-3. The gene orders of the recovered viruses were verified by amplifying the rearranged portions of the viral genomes using reverse transcription and polymerase chain reaction (PCR) followed by restriction enzyme analysis with a set of enzymes which distinguished the rearranged gene orders (FIGS. 5A and 5B).

Example 3

Single-cycle Virus Replication

Monolayer cultures of $10^6$ BHK-21, BSC-40 or BSC-1 cells were infected with individual viruses at an input multiplicity of 3. Following a one hour adsorption period, the inoculum was removed, cultures were washed twice, fresh media was added and cultures were incubated at 31° C. or 37° C. Samples were harvested at the indicated intervals over a 36 hour period and viral replication quantitated by plaque assay on confluent monolayers of BSC-40 cells.

Example 4

Analysis of Viral RNA and Protein Synthesis

Confluent monolayer cultures of BHK-21 cells were infected with individual viruses at an input multiplicity of 5 PFU per cell and given a one hour adsorption period. For analysis of viral RNA synthesis, cultures were treated with actinomycin D (5 $\mu$g/ml) at 1.5 hours post-infection for 30 minutes prior to addition of [$^3$H]-uridine (30 $\mu$Ci/ml) for a 2 or 4 hour labeling period. Cells were harvested, cytoplasmic extracts prepared and RNA analyzed on 1.75% agarose-urea gels as described (Pattnaik and Wertz, 1990). Protein synthesis was analyzed at four hours post-infection by addition of [$^{35}$S]-methionine (40 $\mu$Ci/ml) for a 30 minute labeling period following a 30 minute incubation in methionine free media. Cytoplasmic extracts were prepared and proteins analyzed on 10% polyacrylamide gels as described previously (Pattnaik and Wertz, 1990). Individual RNAs or proteins were quantitated by densitometric analysis of autoradiographs using a Howteck Scanmaster 3 with Pdi Quantity One software and molar ratios were subsequently calculated.

Example 5

Virulence in Mice

The lethality of individual viruses was measured in male Swiss-Webster mice, 3–4 weeks old, obtained from Taconic Farms. Groups of 5–6 lightly anesthetized (Ketamine/Xylazine) animals were inoculated with diluent (PBS) or with serial ten-fold dilutions of individual viruses by either the intracranial route in a volume of 30 $\mu$l or by the intranasal route in a volume of 15 $\mu$l. Animals were observed daily and the 50% lethal dose ($LD_{50}$) for each virus was calculated by the method of Reed and Muench (1938).

Example 6

Protection of Mice

Groups of control mice inoculated with diluent or inoculated intranasally with non-lethal doses of individual viruses were monitored by tail bleeds for neutralizing serum antibody production. On day 14 post-inoculation, mice were challenged with $1.3\times10^6$ PFU of wild-type virus (designated N1) administered intranasally in 15 $\mu$l while under light anesthesia as above. Challenged animals were observed for 21 days.

Example 7

A General Approach to Rearranging the Genes of the Mononegavirales

To rearrange the genes of VSV without introducing any other changes into the viral genome, the polymerase chain reaction (PCR) was used to construct individual cDNA clones of the N, P, M, and G genes flanked by sites for restriction enzymes that cut outside their recognition sequences. To flank the P, M, and G genes, BspM1 sites were used, whereas to flank the N gene, Bsa1 sites were used (N contains an internal BspM1 site). PCR primers were designed to position these restriction sites so that the four-base cohesive ends left after endonuclease digestion corresponded to the ACAG sequence of the conserved 5' AACAG . . . 3' that occurs at the start of each VSV mRNA (see also FIG. 3A). For example: 5' . . . ACCTGCACT A <u>ACAG</u> . . . AAAAAAACTA<u>ACAG</u>AGATGCAGGT . . . 3' (SEQ ID No. 1), where the VSV sequence, written in the positive sense, is in italics, the BspM1 recognition sites are in bold letters, and the four-base cohesive ends left by BspM1 digestion are underlined. In this way, the four genes, together with their respective intergenic junctions, were recovered on individual DNA fragments that had compatible cohesive termini (FIGS. 3A and 3B). The only deliberate departure from the wild-type sequence was that the untranscribed intergenic dinucleotide was made 5'-CT-3' at all junctions, including that following the P gene where the wild-type sequence is 5'-GT-3'. This mutation is apparently silent (Barr et al., 1997). To circumvent the effect of spurious mutations arising during PCR, the termini of the cloned genes were sequenced and their interiors were replaced with corresponding DNA fragments from the infectious clone.

Two other starting plasmids were required to reconstruct the rearranged full-length clones: one contained a bacteriophage T7 promoter followed by the VSV leader sequence, with a unique BspM1 site positioned to cut within the 5' (A)ACAG at the start of the N gene: 5' . . . GAAACTTTA <u>ACAGT</u>AATGCAGGT . . . 3' (SEQ ID No. 2). The other plasmid contained the first 420 nucleotides of the L gene and had a unique BspM1 site positioned to cut within the same sequence at the start of L: 5' . . . ACCTGCACTA<u>ACAG</u>CAATCATG . . . 3' (SEQ ID No. 3). The N, P, M and G gene fragments were ligated unidirectionally into the unique BspM1 sites of these plasmids to rebuild the viral genome in a stepwise manner from either the 3' or the 5' end. Insertion of each gene recreated a wild-type intergenic junction and left a unique BspM1 site to receive the next gene.

Figure 9:
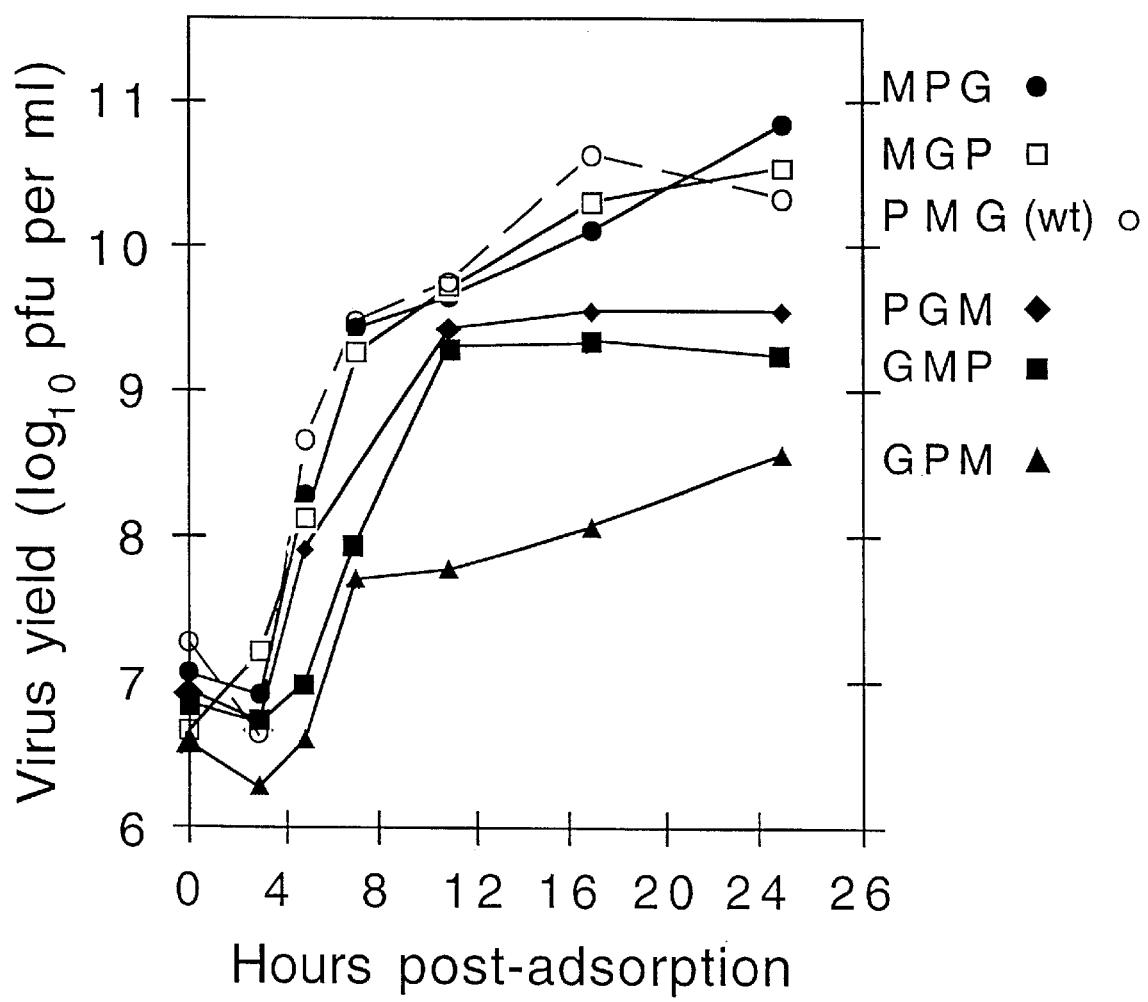
FIG. 9 shows the single step growth curves of wild type VSV and the rearranged variants in BSC-1 cells. Viral titers were measured in duplicate at each time point during three independent single-step growth experiments at 37° C., and the results were averaged.

The final step of plasmid construction was to add a DNA fragment from the infectious clone that encompassed the remaining 6 kb of the L gene, the 5' end of the viral genome, and the ribozyme and T7 terminator that are needed for the intracellular synthesis of replication-competent transcripts (Pattnaik et al., 1992). This approach can be applied to any of the Mononegavirales which have conserved sequences at their intergenic junctions. The rearranged gene orders that were created in this manner are shown in FIG. 1. To validate this cloning strategy and to verify that the individual genes encoded functional proteins, a plasmid that contained the wild-type genome was created in parallel with the rearranged cDNA clones. Virus recovered from this plasmid was used as the wild-type (N1, see FIG. 1). In all cases, the conserved 23 nucleotide intergenic region was maintained between genes.

Example 8

Generation of Viruses with Rearranged Genomes

Initial rearrangements of the cDNA of the genome of VSV were conservative, in light of the highly conserved nature of the genomes of all viruses in the family Mononegavirales, and the knowledge that precise molar ratios of the VSV nucleocapsid (N) protein, phosphoprotein (P) and RNA polymerase (L) protein are required for replication. The 3' most gene, N, and the 5' most gene, L, were originally maintained in their natural positions and the three central genes of VSV, the P, M and G genes, were rearranged in all possible combinations to generate the 6 genome orders (N1 (wt), GMP, MGP, PGM, GPM and MPG) as shown in FIG. 1. The wild-type gene order, N1, was generated as described above to serve as a test that all of the cDNA elements were functional. Each of the cDNAs was constructed in a specialized T7 expression plasmid designed to generate RNAs having precise 5' and 3' termini (Pattnaik et al., 1992).

The ability of the rearranged cDNAs to generate a functional RNA genome was demonstrated by transfecting each of the six rearranged cDNAs into BHK cells infected with vaccinia virus expressing the T7 polymerase (Fuerst et al., 1986) concomitantly with cDNA clones encoding the VSV N, P, and L proteins to encapsidate the RNA transcribed from the cDNA clones and to form functional ribonucleocapsids as described (Whelan et al., 1995). Virus was recovered with varying efficiency from all six of the cDNA constructs and amplified in the presence of cytosine arabinoside (25 $\mu$g/ml) following filtration through 0.2 $\mu$m filters to remove the recombinant vaccinia virus used to express the T7 polyrnerase required for transcription of the cDNAs to yield RNA virus.

Example 9

The Gene Order of the Recovered RNA Viruses Reflects That of the cDNA From Which They Were Generated The gene orders of the recovered viruses were determined after three passages in cell culture by amplifying a 4.1-kb fragment encompassing the rearranged portions of the viral genomes by reverse transcription and PCR, followed by restriction enzyme analysis of the PCR products. PCR was carried out with primers located in the N and L genes. After cleavage with restriction endonuclease AccI, BglI, or PstI, which cleave uniquely in the P, M, or G gene, respectively, the observed sizes of the digestion products were found to be exactly as predicted (FIGS. 5A and 5B). The data showed that the gene orders of the recovered viruses corresponded to the cDNA clones from which there were recovered. There was no evidence for the reappearance of the wild-type gene order among the variants.

Example 10

Synthesis of Viral RNAs and Proteins

The recovered viruses were next examined for their levels of gene expression. Synthesis of viral RNAs and proteins by the variant viruses was examined by metabolic incorporation of [$^3$H]uridine or [$^{35}$S]methionine into infected cells, and analysis of the radiolabeled products by gel electrophoresis. The same species of viral RNAs were made in cells infected with the wild-type virus and with each of the variants: the 11.16-kb genomic RNA and mRNAs representing the L, G, N, P, and M genes (FIG. 6). The latter two mRNAs are similar in size and comigrated during electrophoresis. No novel or aberrant RNA species were found in cells infected with the variant viruses, showing that the virus preparations were free of DI particles (FIG. 6). Moreover, the similarities among the RNA patterns reinforced the idea that the behavior of the viral polymerase during transcription across the intergenic junctions was determined exclusively by local sequence elements at these positions, with no detectable long-range influences. In accordance with the RNA patterns, the viral proteins made by the variant viruses also resembled qualitatively those made during wild-type infection (FIG. 7).

Although the RNA and protein profiles of cells infected with the wild-type and variant viruses were qualitatively similar, measurement of the relative levels of the different RNAs and proteins showed that the variant viruses expressed their genes in molar ratios that differed from both the wild type and one another (FIGS. 8A and 8B). Normalizing the expression of each protein to that of the promoter-proximal N gene for each variant virus showed that the relative expression level of a gene depended primarily on its location in the genome and thus on its distance from the promoter, just as predicted by the model of progressive transcriptional attenuation. This is clearly exemplified by comparison of the molar rations of proteins expressed by the wild-type (PMG) with variant GMP in which the order of the internal genes is reversed (FIGS. 8A and 8B). A similar quantitative analysis of the mRNA profiles was complicated by the lack of resolution of the M and P mRNAs (FIG. 6), but measurement of the L, G, and N mRNA levels reinforced the conclusion that the proximity of a gene to 3' end of the viral genome was the major determinant of its level of transcription. For example, the differences in the relative abundance of G mRNA reflected the position of the G gene (FIG. 6). The RNA profiles also showed that the level of RNA replication, as measured by the abundance of the 11.1-kb genomic and antigenomic RNAs, differed substantially among the variants (FIG. 6).

Example 11

Replication of Viruses with Rearranged Genomes

The variant viruses were compared for their ability to replicate under the conditions of plaque formation and single-cycle growth. Although some of the viruses such as MGP and MPG were indistinguishable from the N1 wild type virus (PMG) in these assays, others such as GMP, GPM, and PGM formed significantly smaller plaques than the wild type on monolayers of BSC-1 cells (Table 1). Moreover, GMP plaques ceased to grow after 24 h when those of the wild type virus and the other variants were still increasing in size (Table 1). The impaired replication of GMP, GPM, and PGM was also demonstrated during single-cycle growth on BSC-1 cells (FIG. 9). At 17 h post-infection, the incremental yields of the variants averaged over three independent growths and expressed as percentages of the wild type were as follows: for MGP, 107%; for MPG, 51%; for GMP, 23%; for PGM, 21%; and for GPM, 1.6% (Table 2).

TABLE 1

| | Plaque diameter (mean ± standard error)[a] | |
|---|---|---|
| Virus | 24 h | 30 h |
| PMG (wild type) | 4.02 ± 0.12 | 4.81 ± 0.19 |
| GMP | 3.08 ± 0.17 | 3.10 ± 0.18 |
| MGP | 3.96 ± 0.19 | 4.97 ± 0.18 |
| PGM | 3.36 ± 0.12 | 3.86 ± 0.14 |
| GPM | 2.26 ± 0.09 | 3.16 ± 0.13 |
| MPG | 3.85 ± 0.18 | 5.43 ± 0.17 |

[a]Plaque diameters were measured from photographs taken at approximately two-fold magnification of groups of 50 (24 h) or 70 (30 h) viral plaques formed at 37° C. on monolayers of BSC-1 cells.

Example 12

Virulence in Mice

Intracerebral or intranasal inoculation of wild-type VSV into mice causes fatal encephalitis. Since 1938, when Sabin and Olitsky first described the neuropathology and comparative susceptibility of mice to VSV encephalitis as a function of age and route of inoculation, young mice have served as a convenient and sensitive small animal model for comparing the lethality of VSV and its mutants (Sabin and Olitsky. 1938; Wagner, 1974). The pathogenesis of the variant viruses in mice was therefore examined.

Figure 5A:
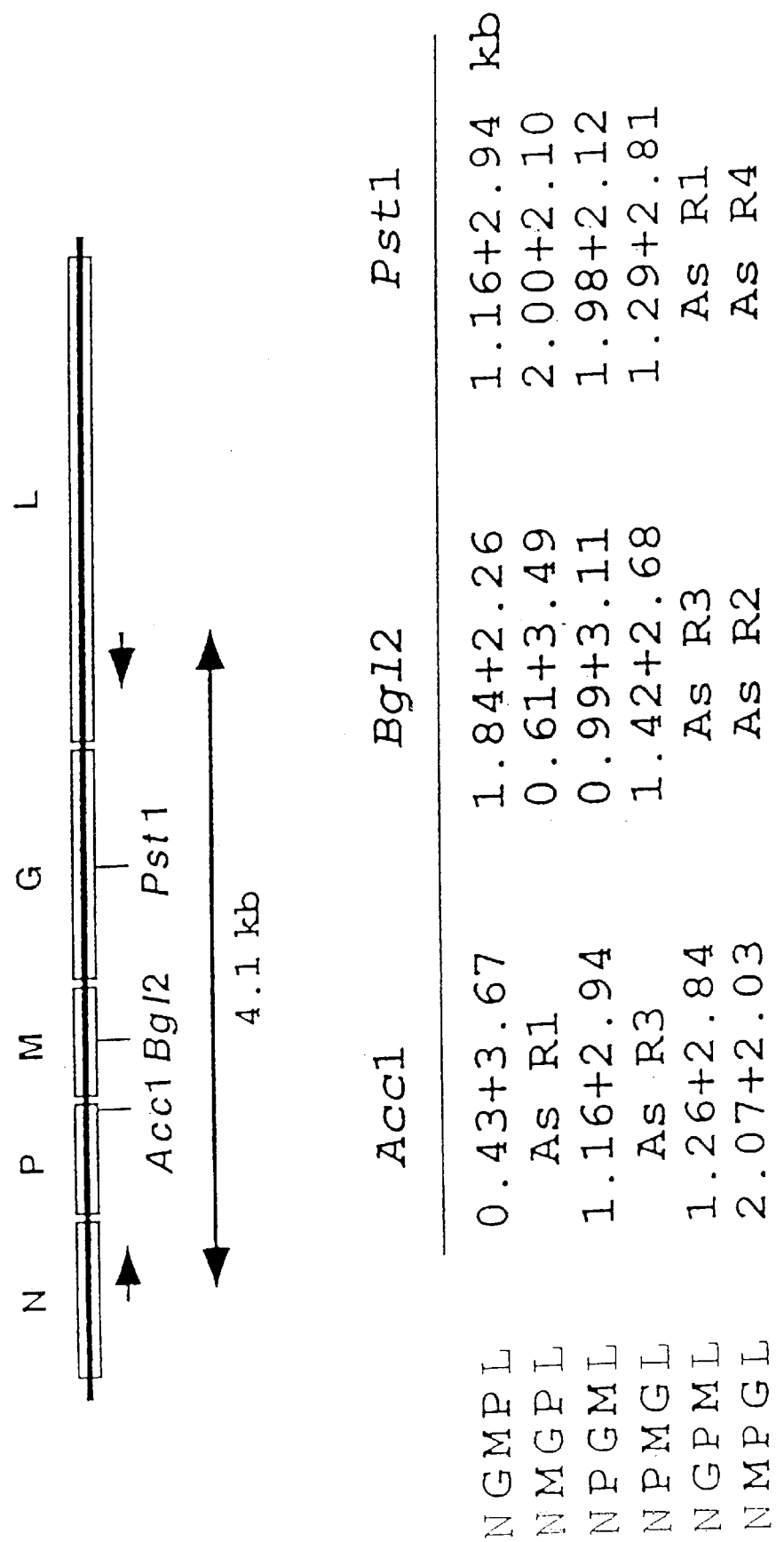
FIG. 5A shows the schematic diagram of the VSV genome showing positions of PCR primers that annealed to the N or L genes, respectively (shown by the arrows) and restriction enzyme cleavage sites and predicted fragment sizes.
Figure 5B:
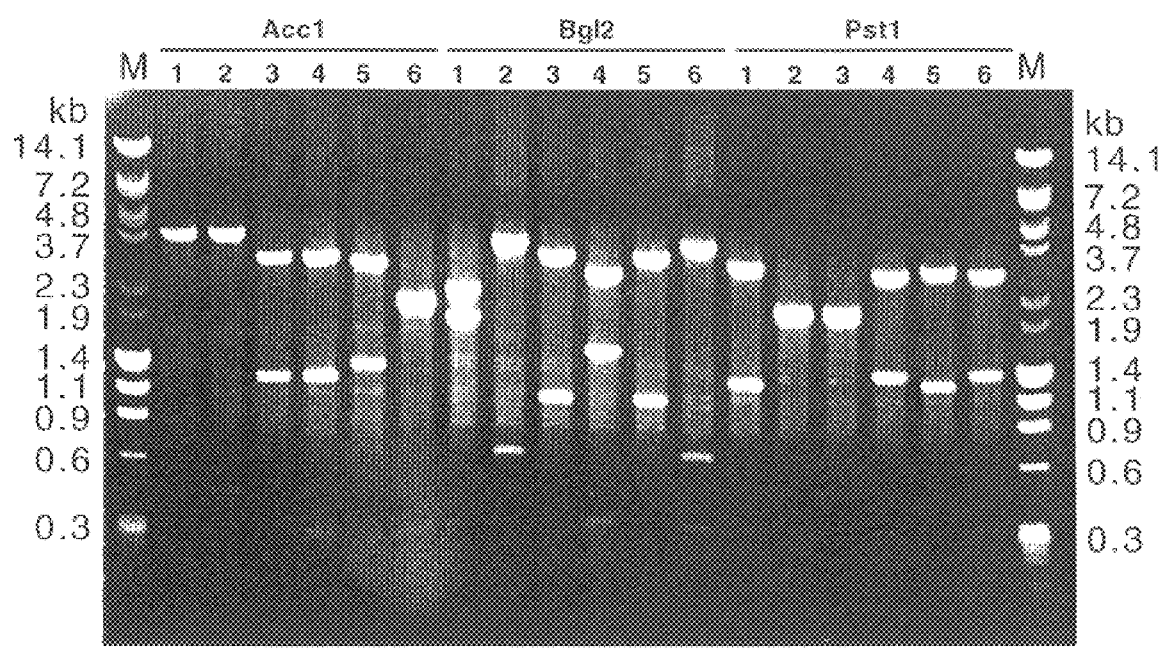
FIG. 5B shows the products after digestion with indicated enzymes of the cDNAs of viral RNA from viruses GMP, MGP, PGM, PMG, GPM and MPG (lanes 1–6, respectively). Fragments were analyzed by electrophoresis on a 1% agarose gel in the presence of ethidium bromide. Lane M=marker DNA fragments with sizes as indicated.
Figure 6:
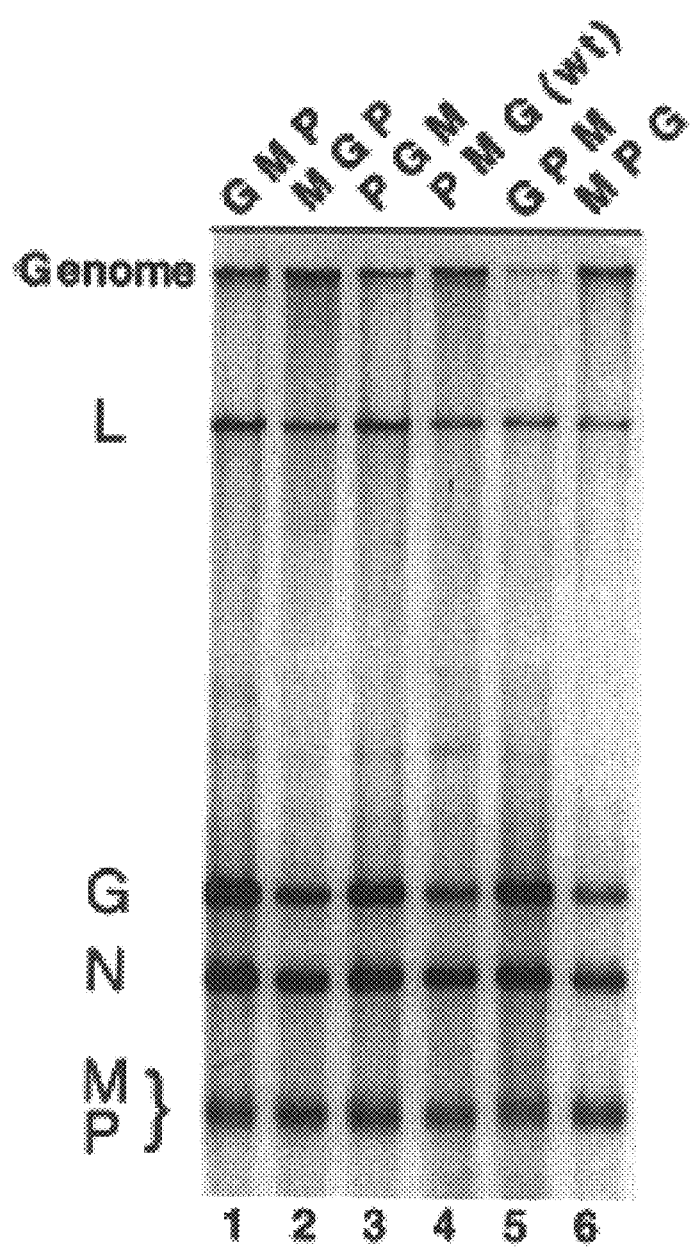
FIG. 6 shows viral RNAs synthesized in BHK-21 cells that were infected with the wild-type and variant viruses. Viral RNAs were labeled with [$^3$H]uridine, resolved by electrophoresis on an agarose-urea gel, and detected by fluorography. The infecting viruses are shown above the lanes, and the viral RNAs are identified on the left.
Figure 7:
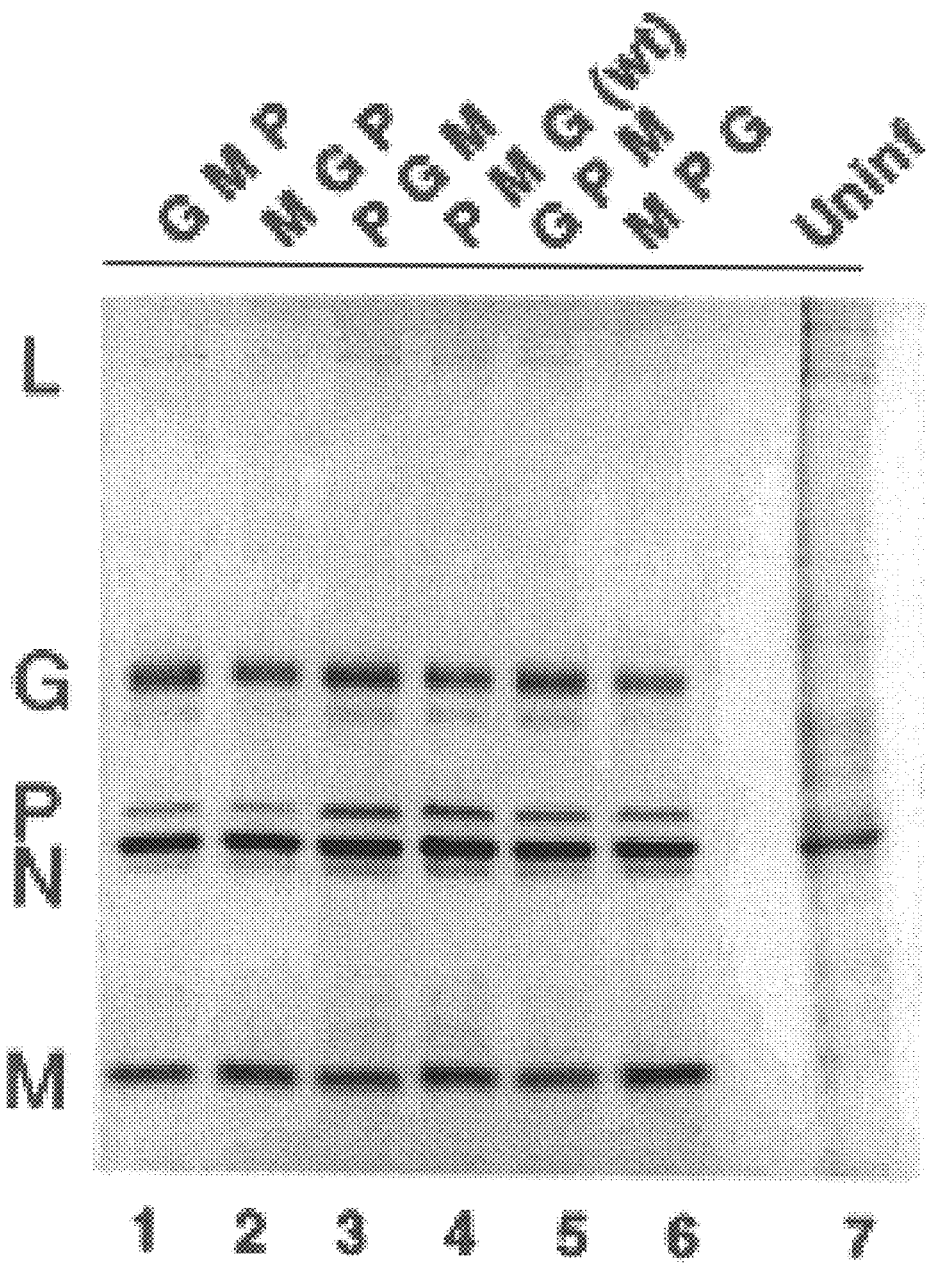
FIG. 7 shows viral proteins synthesized in BHK-21 cells that were infected with the wild-type and variant viruses. Viral proteins were labeled with [$^{35}$S]methionine, resolved by electrophoresis on an SDS-polyacrylamide gel, and detected by autoradiography. The infecting viruses are shown above the lanes, and the viral proteins are identified on the left. Uninf, uninfected cells.
Figure 8A:
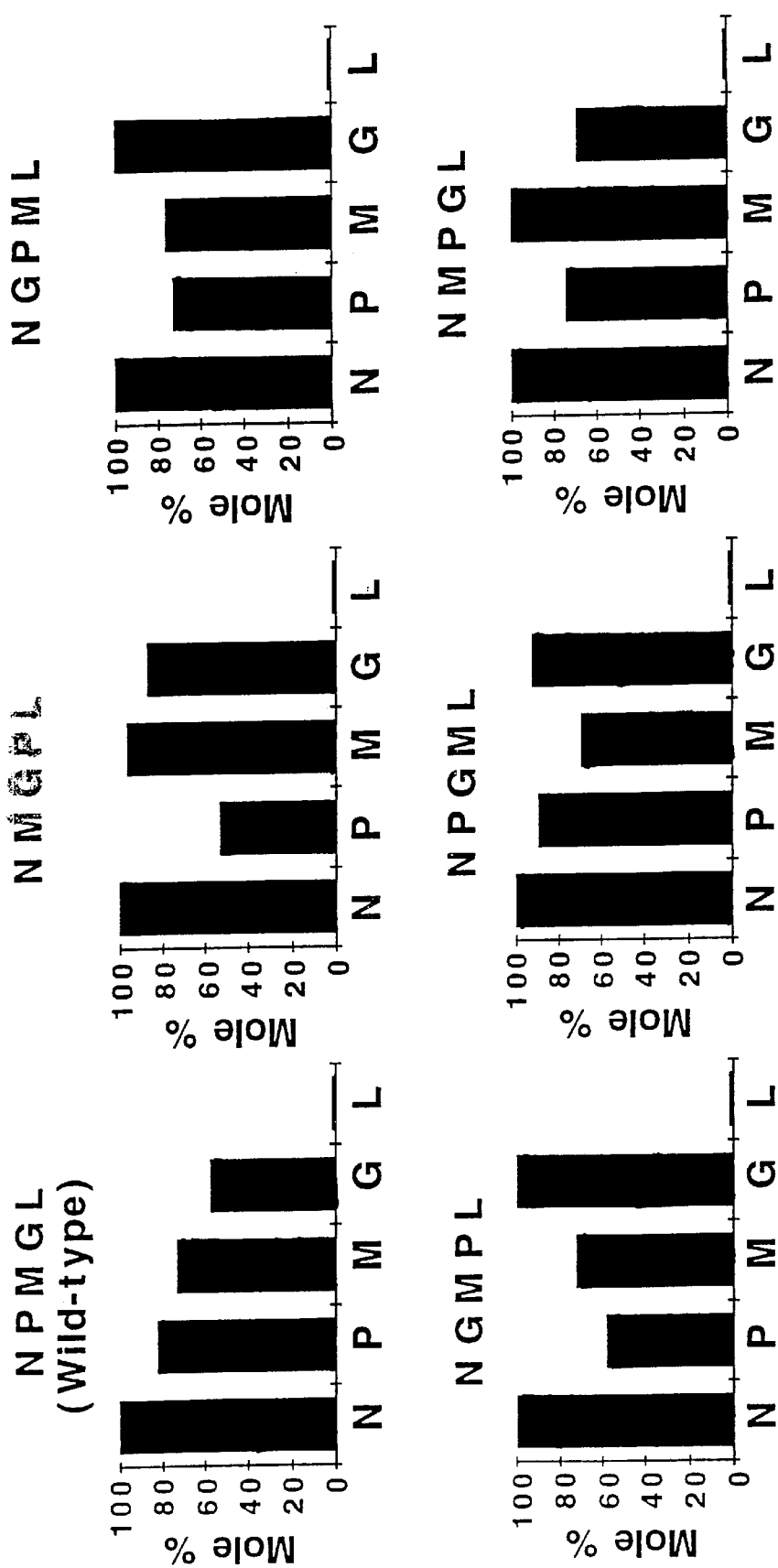
FIGS. 8A and 8B show the molar ratios of proteins synthesized in BHK-21 cells that were infected with the wild type and variant viruses. Proteins were labeled, resolved on SDS-polyacrylamide gels as shown in FIG. 7, and quantitated by phosphorimaging. Molar ratios were calculated after normalizing for the methionine contents of the individual proteins: N-14, P-5, M-11, G-10 and L-60.
Figure 8B:
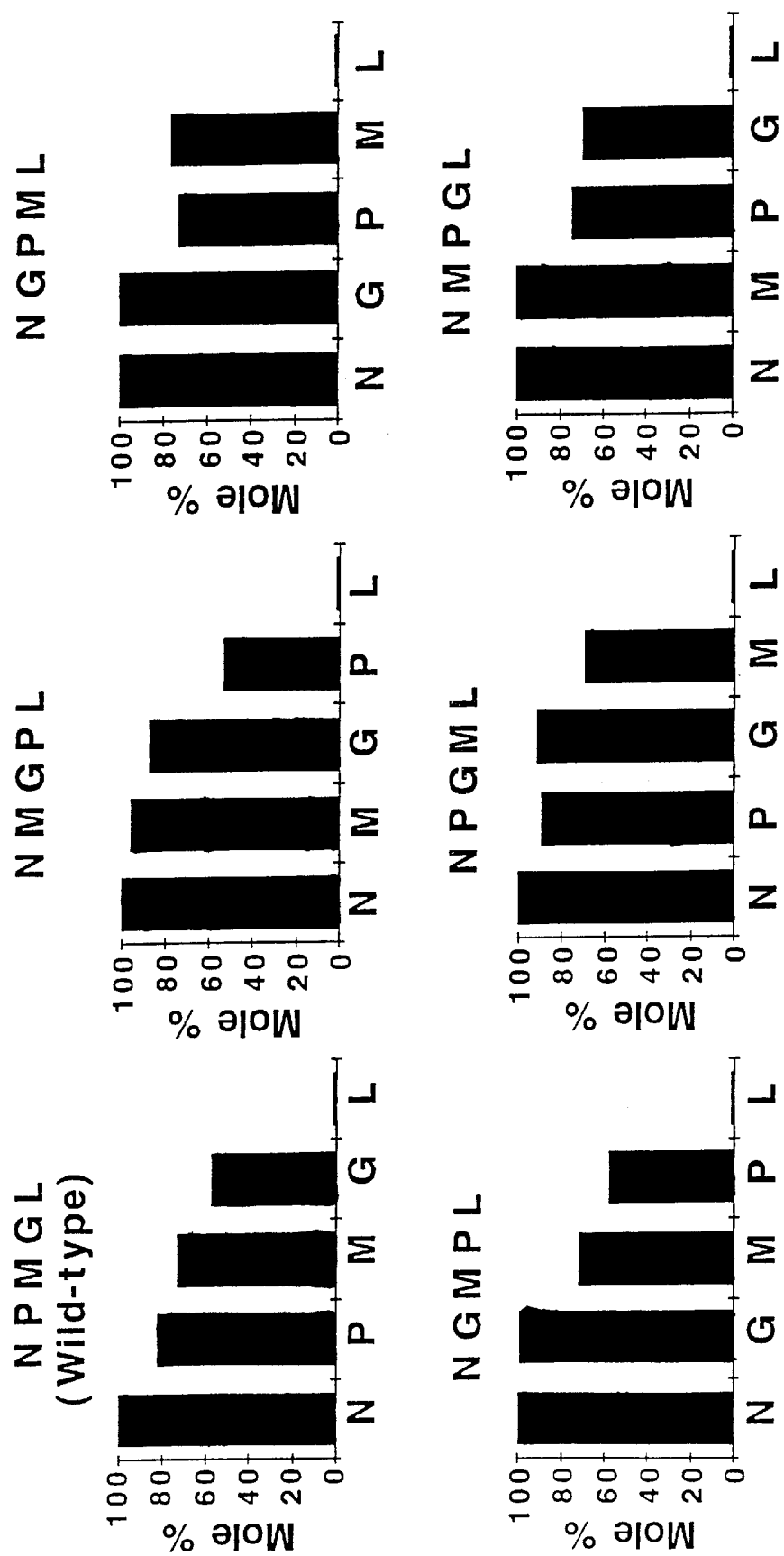

Intranasal inoculation of wild-type VSV into 3–4 week old mice causes encephalitis, paralysis and death after 7–11 days (Sabin and Olitsky, 1938), with the $LD_{50}$ dose being about 10 PFU. The virulence of the variant viruses was compared by inoculating groups of mice intranasally with serial 10-fold dilutions ranging from 0.1 to 1,000 PFU per dose and observing them twice daily. Viral gene orders were verified on viruses recovered shortly after death from the brains of inoculated mice by using the methodology shown in FIGS. 5A and 5B. In each case, the gene order of the recovered virus corresponded to that of the inoculum (data not shown).

Figure 10:
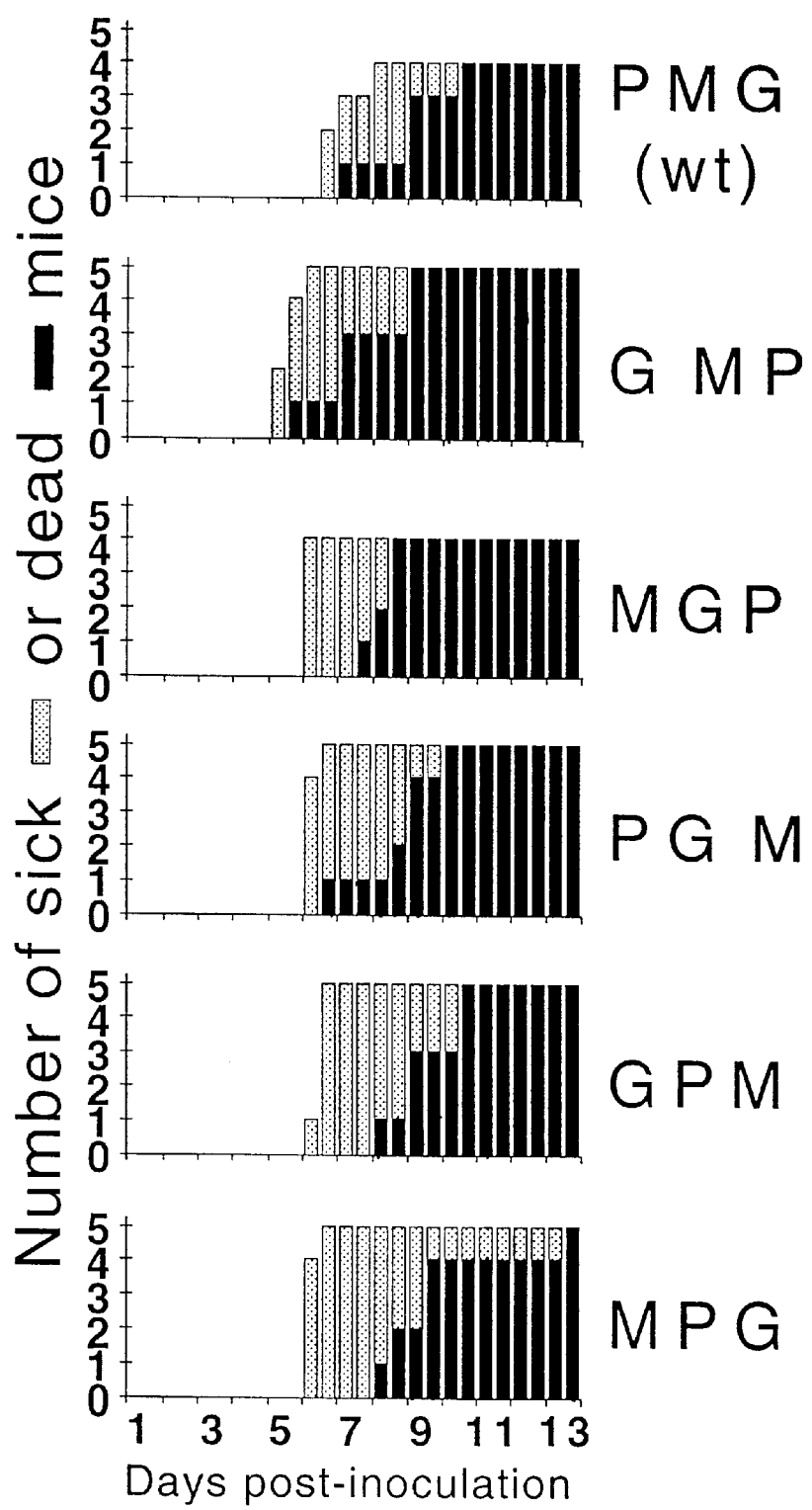
FIG. 10 shows pathogenesis of wild-type (wt) and variant viruses following intranasal inoculation into mice. The time course of morbidity (gray bars) and mortality (black bars) in animals that received intranasal inoculation of 100 PFU of each of the variant viruses is shown. No further changes occurred after the time periods shown.

The $LD_{50}$ doses for the variant viruses were similar to that of the wild type, with viruses GPM, GMP, and MGP requiring slightly higher (1.5- to 2-fold) dose (Table 2). These experiments were repeated three times, and the results of a representative experiment show the time of appearance of illness and death at a dose of 100 PFU per mouse (FIG. 10). The wild-type infected animals first appeared sick at 6 days post-inoculation, rapidly became paralyzed, and died within two weeks. Recombinants GMP and MGP elicited reproducibly faster pathogenesis, with symptoms developing 24–36 h earlier than in wild-type infected animals, whereas the onset of death from infection with MPG and GPM occurred 24 to 36 h later (FIG. 10). In general, the paralysis that is typical of infection with wild-type VSV was less apparent with the variant viruses, but there was no evidence of persistent nervous system disease such as that produced by some M protein mutants (Barr et al., 1997).

Virulence in mice could not be predicted from the cell culture phenotypes of the variant viruses (Table 2). Of the three recombinants whose replication in cell culture was most compromised (GMP, PGM, and GPM), one (GPM) required 2 fold more virus for an $LD_{50}$ than the wild-type and showed slightly delayed killing in mice, whereas GMP induced faster onset of symptoms and death, and PGM was indistinguishable from wild-type. This lack of correlation between the behavior of viruses in cell culture and their properties in animals is a familiar observation among different animal viruses, but is interesting in this context where the only differences between the viruses were the relative levels of wild-type proteins that they expressed.

TABLE 2

Summary of properties of variant viruses

| Gene order | Relative plaque size[a] | Relative burst size[b] | $LD_{50}$ value[c] | Onset of symptoms[d] |
|---|---|---|---|---|
| PMG (wt) | 1.00 | 1.00 | 14 | 6.0 |
| GMP | 0.64 | 0.23 | 21 | 4.5 |
| MGP | 1.03 | 1.07 | 21 | 5.5 |
| PGM | 0.80 | 0.21 | 12 | 5.5 |
| GPM | 0.66 | 0.016 | 30 | 5.5 |
| MPG | 1.13 | 0.51 | 11 | 5.5 |

[a]Measured at 30 h post-infection (see Table 1).
[b]Measured at 17 h post-infection (see FIG. 9).
[c]PFU per mouse inoculated intranasally.
[d]Days after intranasal inoculation of 100 PFU per mouse (see FIG. 10).

Example 13

Effect of Severe Rearrangements on Recovery of Viable Virus

Encouraged by the relative tolerance that VSV exhibited for rearrangement of the three internal genes based on recovery of infectious virus, further rearrangements were made that altered the position of the gene for the nucleocapsid protein, N. The N protein is required in stoichiometric quantities to support encapsidation of nascent genomic RNA during RNA replication (Patton et al., 1984). RNA replication is dependent on constant synthesis of the N protein, and inhibition of N protein synthesis results in cessation of replication. If the level of N protein synthesis were lowered by moving the N gene progressively away from its promoter proximal site (and thus lowering the level of N gene expression), it would therefore result in lowered levels of genomic replication. As such, the genome of VSV was altered at the cDNA level by moving the N gene from the 3' most position, which results in synthesis of the largest amount of N mRNA, to each sequential internal position as shown in FIG. 1 to create N2 (PNMGL), N3 (PMNGL), and N4 (PMGNL). N1 corresponds to the wild-type arrangement. A fourth and fifth variation, in which the G gene was moved from next to last in the order and placed in front of the N gene, were also generated (FIG. 1). This results in G1N2 (GNPML), as well as G1N4 (GPMNL), where the position of the G and N genes were exchanged.

The cDNAs for N1–N4 and G1N2 and G1N4 were transfected into cells as described above and analyzed for the ability to generate viable virus. Virus was recovered with comparative ease from N2, N3 and G1N2. Virus was not recovered from N4 and G1N4, even with repeated trials using standard transfection conditions at 37° C. Virus corresponding to N4 and G1N4 was recovered by lowering the temperature of the transfections and subsequent passages to 31° C.

Example 14

RNA Synthesis by Viruses with N Gene Rearrangements

Figure 11:
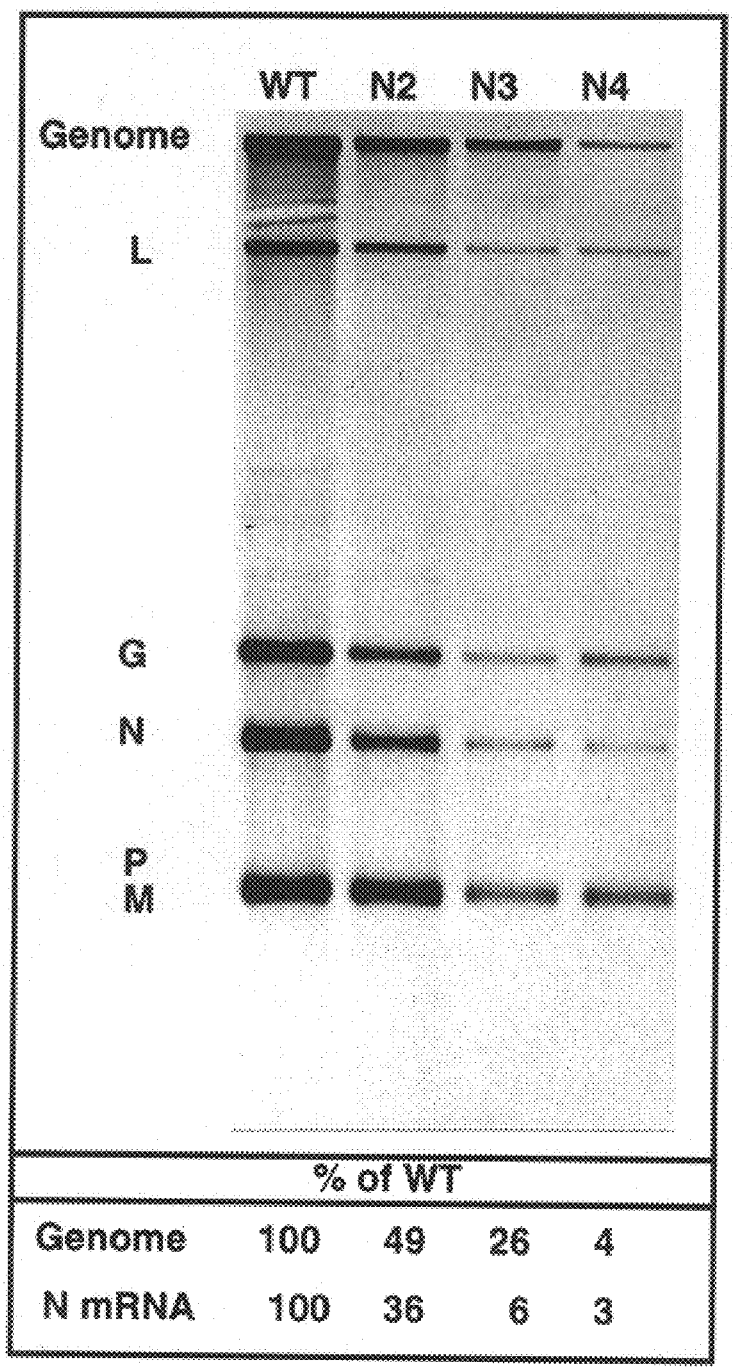
FIG. 11 shows the viral specific RNA synthesized in BHK-21 cells infected with rearranged viruses N1 (wt), N2, N3 and N4. Conditions of infection, labeling and analysis were as described in FIG. 6.

Moving the N gene sequentially down the genome had a marked effect on the level of replication and N mRNA synthesis (FIG. 11). The level of N mRNA synthesis decreased substantially from wild-type levels as the N gene was moved successively away from the promoter in viruses N2, N3 and N4 (36%, 6% and 3% of wild-type, respectively; FIG. 11). Consistent with this, an increase in the amount of G mRNA was observed with virus N4, in which the G gene was moved one position closer to the promoter as the N gene replaced it as next to last in the gene order (FIG. 11). The amount of genomic RNA replication of N2, N3 and N4 declined relative to wild-type (50%, 28% and 4%, respectively; FIG. 11), concomitant with the lowered expression of the N gene, as predicted if N protein synthesis was limiting for replication. The overall level of transcription was reduced also as the N gene was moved progressively promoter distal, presumably as a secondary effect due to the lowered number of genomic templates.

Example 15

Protein Synthesis of Viruses with the N Gene Rearranged

Figure 12:
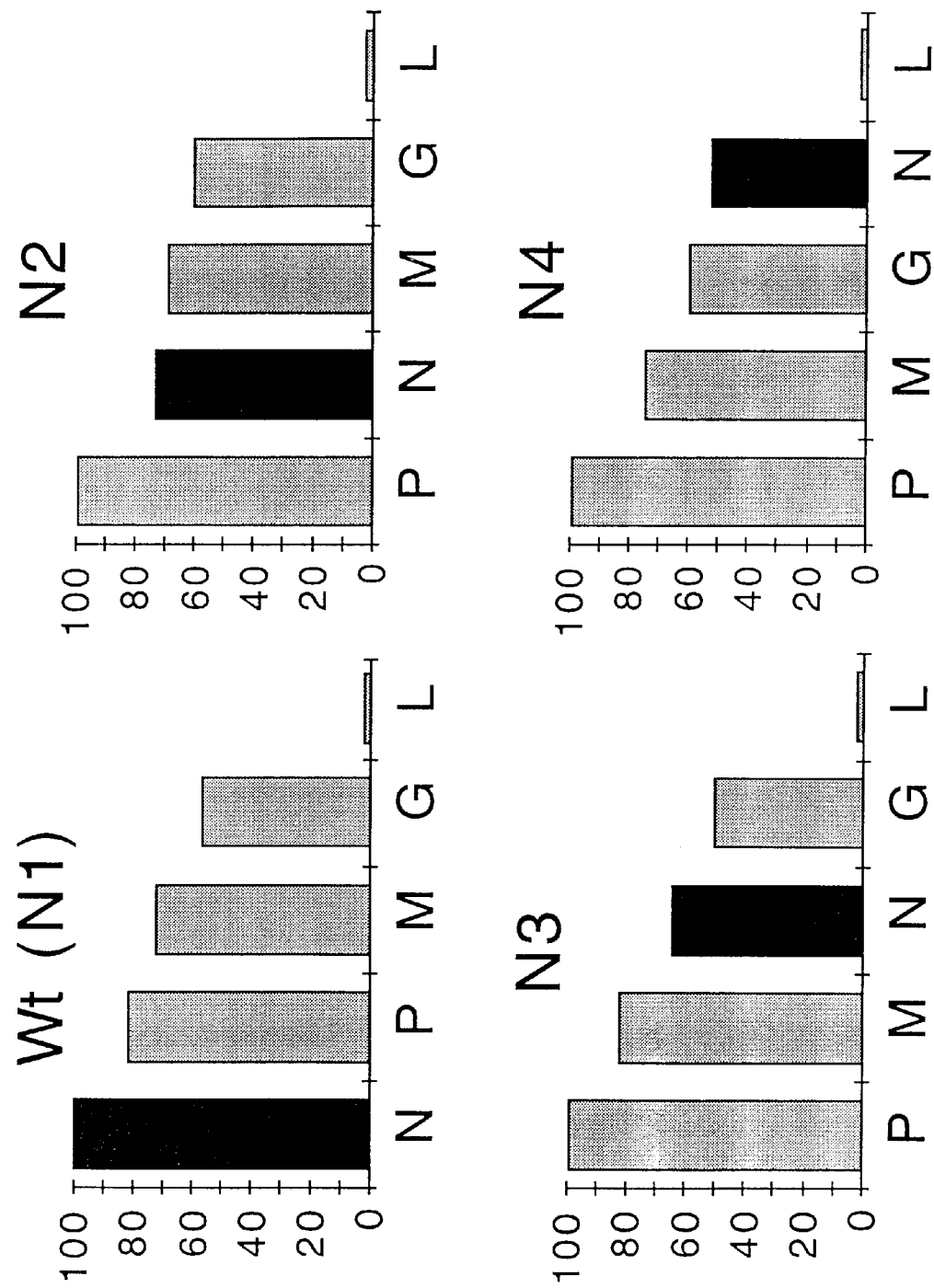
FIG. 12 shows the molar ratios of the VSV specific proteins synthesized in BHK-21 cells following infection with rearranged viruses N1 (wt), N2, N3 and N4. Proteins were analyzed as described in FIG. 7 and molar ratios calculated as described in FIG. 8.

All five of the VSV proteins were expressed in cells infected with the rearranged viruses and they all co-migrated with those of the wild-type virus. However, N protein synthesis declined as its gene was moved away from the 3' position. The data presented in FIG. 12 show how the molar amounts of the proteins decrease as a function of their distance from the 3' terminus in the wild-type virus N1. When the N gene was translocated, the data in FIG. 12 show that the molar ratios of the N protein relative to the phosphoprotein P decreased progressively as the N gene was moved from first to second, third, or fourth in the gene order. These results confirm the predictions from previous analysis of gene expression in VSV and the sequential nature of transcription. Moreover, these data demonstrate directly that the position of a gene determines its level of expression. Examination of the levels of proteins in isolated, mature N1–N4 virions showed that the relative molar ratios of the proteins in mature virus particles remained essentially the same as that of the wild-type virus. However, less overall virus was produced from infections of N2–4, correlating with the lowered level of genomic RNA replication.

Example 16

Replication Ability in Cell Culture

Figure 13:
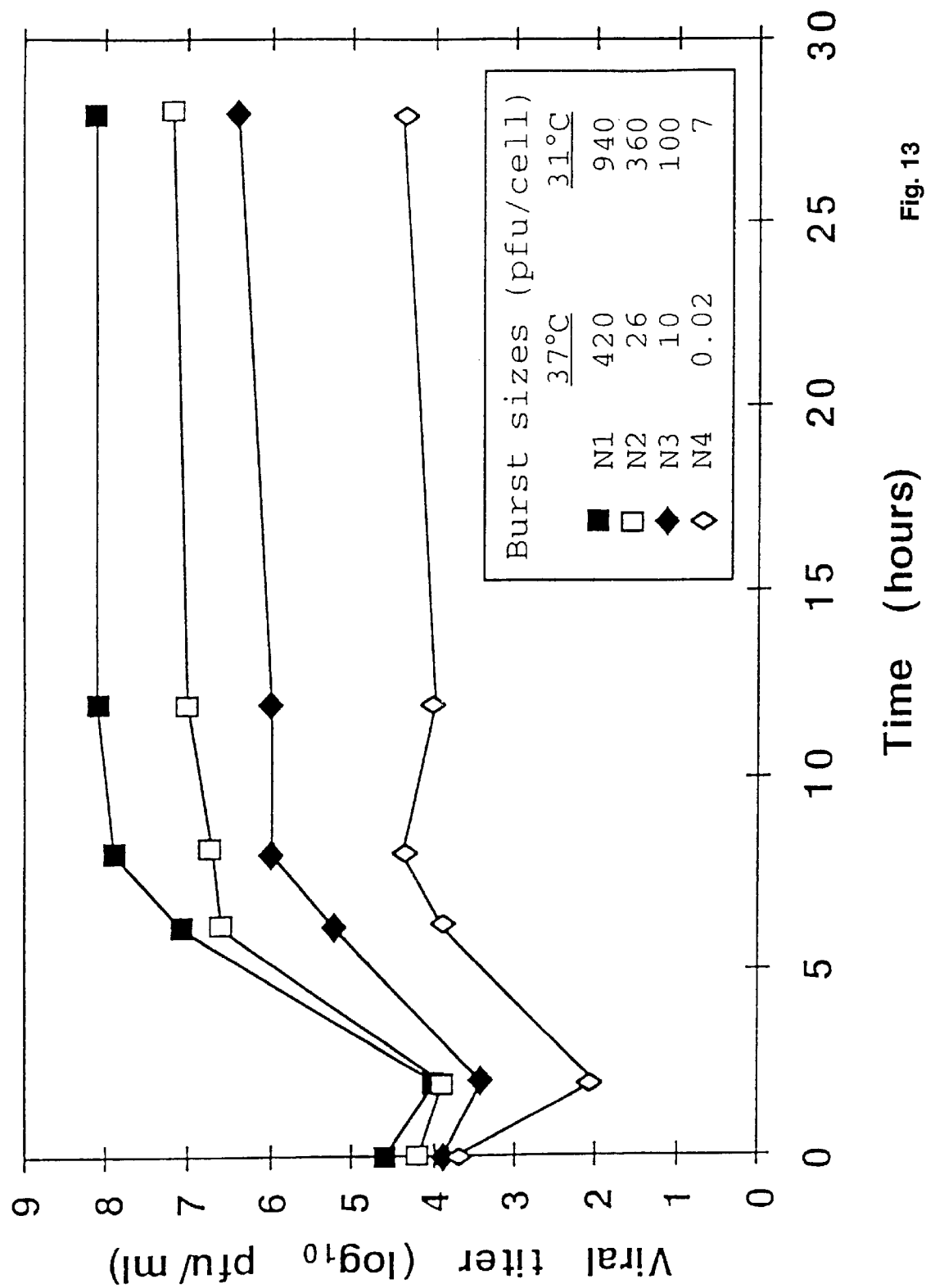
FIG. 13 shows replication of viruses with N gene translocations by single step growth in BHK cells.

Viruses with the N gene rearrangements replicated progressively less well as the N gene was moved downstream of its normal promoter proximal position. Growth potential was analyzed by single step growth curves. N2 and G1N2 were reduced in viral yields by approximately 15-fold at 37° C; N3 was reduced by 50 fold and N4 was reduced by 20,000 fold in replication ability as compared to the wild-type virus (FIG. 13). Comparison of virus growth at 31° C. showed a similar progressive decline, however, the effect was less pronounced than at 37° C., and overall, this temperature was more permissive for growth (FIG. 13, inset). At 31° C., N4 replication was reduced approximately 100 fold compared to wild-type. The burst size in PFU per cell for each of the viruses at 31° C. and 37° C., shows that the yield per cell declined in a stepwise manner as the N gene was moved to each successive position down the genome (FIG. 13). The relative plaque sizes of the viruses also varied; plaques of N4 are compared to that of wild-type (<0.5 mm compared to 3 mm in diameter at 42 hours post infection). These data indicate that although the genes of N2, N3 and N4 were wild type, rearrangement of the genes and the subsequent alterations of the protein molar ratios rendered some step of the viral replication process partially temperature sensitive.

Example 17

Lethality in Mice

Growth of VSV in mice, neuropathology and susceptibility to encephalitis by intracerebral or intranasal inoculation of wild-type, temperature sensitive or plaque size variant viruses has been described in detail (Sabin and Olitsky, 1937; Shechmeister et al., 1967; Wagner, 1974; Youngner and Wertz, 1968). The lethality of viruses N2, N3 and N4 for mice was examined in comparison with the wild-type virus N1 for both the intracerebral and intranasal routes of inoculation. The amounts of virus required for a lethal dose ($LD_{50}$) by each route is shown in Table 3. By intercerebral inoculation, the $LD_{50}$ dose for each of the viruses was 1 to 5 pfu, although the average time to death was about twice as long with the N4 virus. These data show that when injected directly into the brain, thereby circumventing the majority of host defenses, the rearranged viruses eventually could cause fatal encephalitis.

Figure 14:
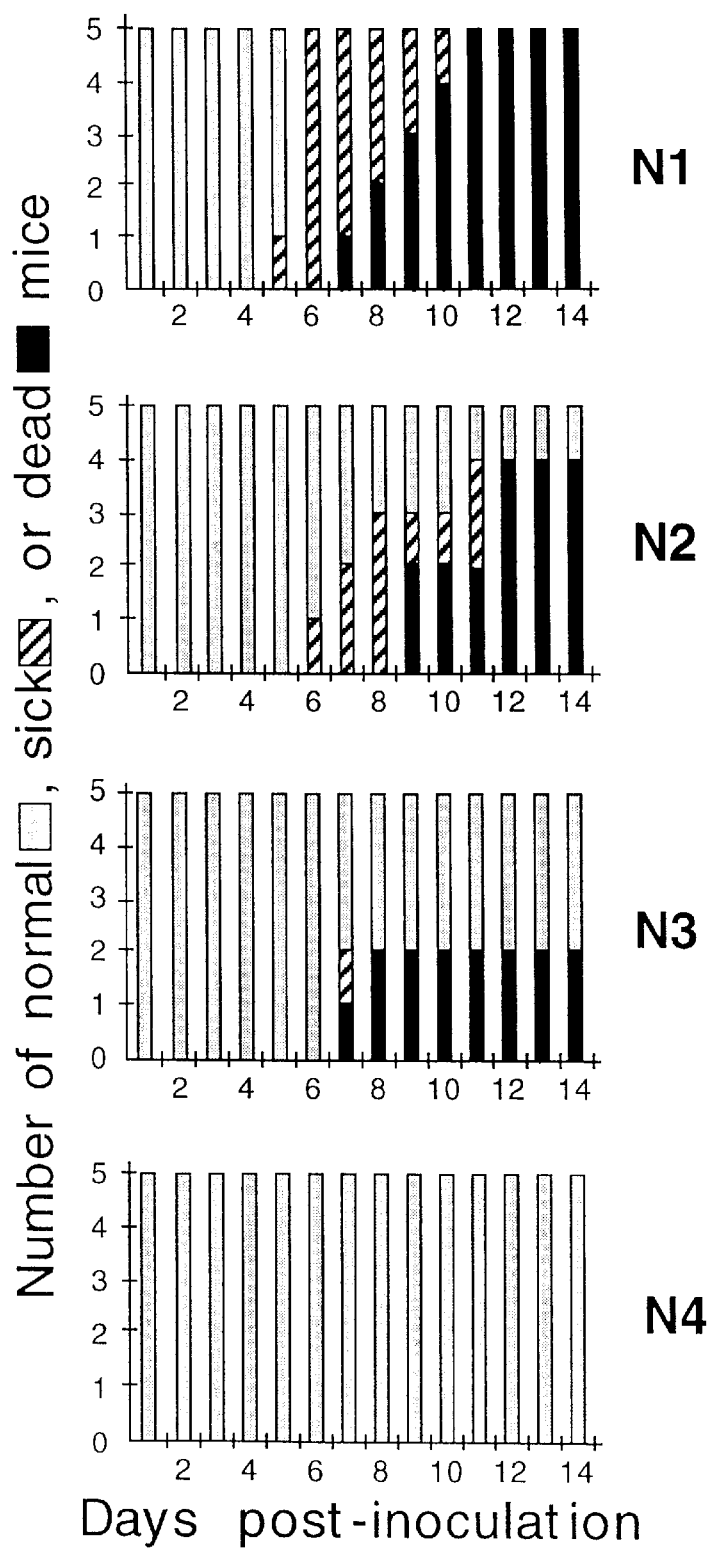
FIG. 14 shows relative lethality of viruses N1 (wt), N2, N3 and N4 for mice.

Intranasal inoculation, by contrast, showed striking differences in the amount of virus required for a lethal dose (Table 3). Whereas the $LD_{50}$ dose for the wild-type virus by IN administration was approximately 10 pfu, the values for N2, N3 and N4 viruses were progressively greater. N2 required 20 fold more virus, N3, 500 fold more virus, and N4 required 3000 fold more virus than wild-type, i.e. 30,000 PFU for the $LD_{50}$. The time to onset of sickness (ruffled fur, lethargy, hind limb paralysis) and extent of death increased progressively compared to wild-type following infection with viruses N2, N3 and N4 (FIG. 14) and the extent of mortality was a function of dose (Table 3). These data show that when administered by a peripheral route, the progressive reduction in virus replication observed in cell culture correlated with a reduced lethality in mice.

TABLE 3

Lethality of wild-type or Rearranged VSV Viruses for Mice

| | $LD_{50}$ Data* pfu/mouse (Average days to death) | |
|---|---|---|
| | Intracranial | Intranasal |
| N1 NPMGL (WT) | 1 (3–6) | 11 (5–10) |
| N2 PNMGL | 5 (3–7) | 250# (9–12) |
| N3 PMNGL | 5 (3–8) | 5,400# (7–9) |
| N4 PMGNL | 1 (4–11) | 30,000 (10–12) |

*The $LD_{50}$ for each route of inoculation was calculated from mortality among groups of 5 to 7 mice inoculated either IC or IN with five serial 10-fold dilutions of virus. Data from a single internally controlled experiment are shown; the duplicate experiments carried out for each route of administration were similar.
Mortality data for this virus yielded a bell shaped death curve; the $LD_{50}$ dose was calculated from the lower part of the curve. Days to death are shown in parentheses.

Example 18

Ability of Rearranged Viruses to Protect Against Wild-type Challenge

Figure 15:
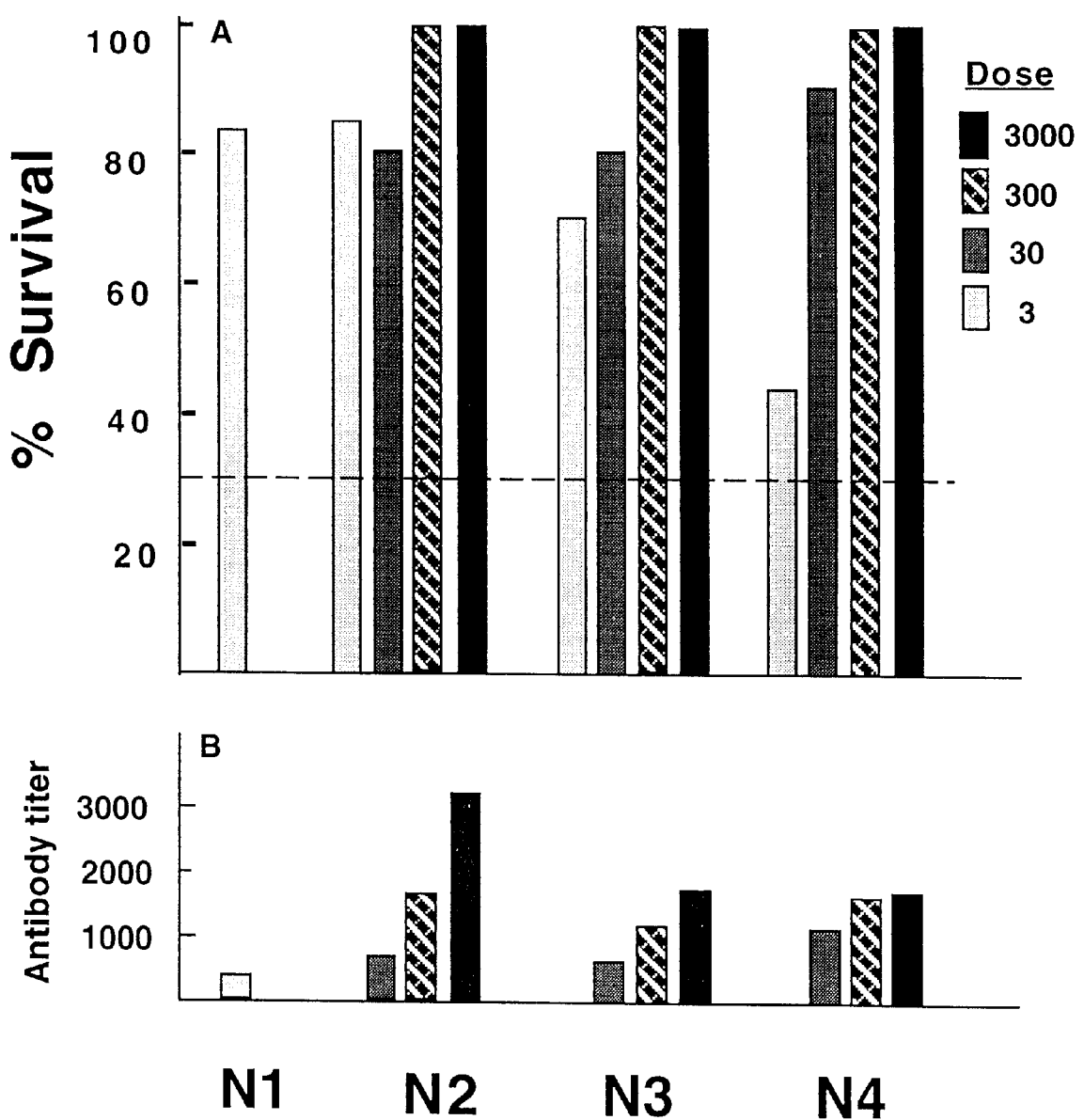
FIG. 15 shows a comparison of antibody production and ability to protect against lethal challenge for viruses N1 (wt), N2, N3 and N4.

The observation that all of the viruses were lethal when inoculated IC indicated that even the most attenuated viruses were able to replicate in mice. This, coupled with the attenuation observed following intranasal administration, raised the possibility that the attenuated viruses might nevertheless be able to elicit a protective immune response. To test this possibility, mice were immunized by IN inoculation with serial ten-fold dilutions of the wild-type N1 or with variant viruses N2, N3 or N4. The surviving animals were challenged 14 days later by IN inoculation with $1.3 \times 10^6$ PFU of wild-type virus. The percentage of animals surviving the challenge was a function of the immunizing dose in agreement with previous studies (Wagner, 1974). For viruses N2, N3 and N4, 300 PFU per mouse was the lowest dose giving 100% survival; 30 PFU yielded 80–90% survival; 3–6 PFU gave 45–85% survival; and doses below 3–6 PFU per mouse gave results that were not significantly different from those of age matched unimmunized controls (FIG. 15, dotted line in panel A). With the wild-type virus, the lethal dose and the protective dose were close, but in general, 80–85% of animals that survived administration of 3–6 PFU of virus were protected.

Measurement of serum antibody prior to challenge on day 14 showed that despite attenuation for virulence in mice, the level of neutralizing antibody present in the serum of animals immunized with viruses N2, N3 and N4 was higher than that observed in the animals surviving inoculation of 3–6 PFU of wild-type virus and generally increased in a dose dependent manner (FIG. 15B). The lethality of the wild-type virus prevented direct comparison of antibody titers at higher doses, however, the neutralizing antibody titers in animals both vaccinated with viruses N1–N4 and then challenged with $1 \times 10^6$ PFU of wild-type virus ranged from 1:625 to 1:3125. These data show that despite their attenuation for replication and lethality in animals, the N-rearranged viruses elicited a protective response that was undiminished compared with that of the wild-type virus.

Example 19

Organization of Genes to Develop an Optimum Vaccine Virus

The present invention illustrates that gene order in the Mononegavirales determines the level of gene expression. Furthermore, these data show that moving the important Nucleocapsid (N) gene away from its normal 3' promoter proximal position provides a means of generating sequentially more attenuated viruses. The maximal level of attenuation occurs when the N gene is placed next to last in the gene order. The highest level of expression occurs from the 3'-most gene. Therefore, in constructing a vaccine vector that is both attenuated and expresses high levels of the antigen involved in protection, the ideal arrangement is a combination of N4 (3'-PMGNL-5') or G1N2 (3'-GNPML-5') or G1N4 (3'-GPMNL-5'). In these constructs, N4 is maximally attenuated and G1N2 yields the greatest levels of the attachment glycoprotein, important for an immune response. Based upon this criteria, G1N4 (3'-GPMNL-5') should be maximally attenuated and yield the highest levels of G protein.

Example 20

A Vaccine Vector Capable of Expressing Additional Foreign Genes so That the Level of the Foreign Gene is Regulated by Position The genome of VSV can accommodate and express additional foreign genes if inserted at intergenic regions and if the conserved gene start, gene end and intergenic regions are maintained (FIG. 16) (Schnell et al., 1996). Additionally, the level of expression of a foreign gene inserted in the VSV genome can be controlled by the position in the genome at which the gene is inserted. A 660 nucleotide sequence of the bacteriophage Phi X174 genome surrounded by the conserved VSV gene start and gene end sequences was inserted into each sequential gene junction of the full length cDNA of the VSV genome in such a manner so as to maintain the conserved intergenic sequences. The gene order of these constructs was respectively: NIP (3'-NIPMGL-5'), PIM (3'-NPIMGL-5'), MIG (3'-NPMIGL-5'), or GIL (3'-NPMGIL-5') where I represents the (I)nserted foreign gene. Virus was recovered from each of the above-mentioned cDNAs by transfection as described above.

Figure 16:
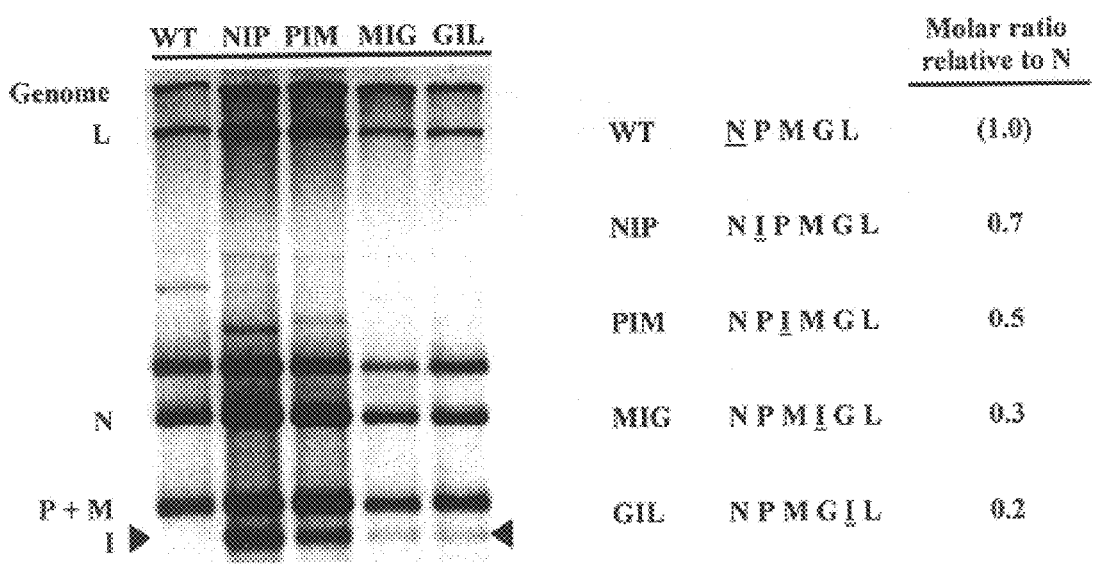
FIG. 16 shows the viral specific RNA synthesized in BHK-21 cells infected with viruses containing a foreign gene (I) inserted at each VSV intergenic junction. Conditions of infection, labeling and analysis are as described in FIG. 6 except the labeling time was from 2 to 4.5 hours postinfection.
Figure 16:
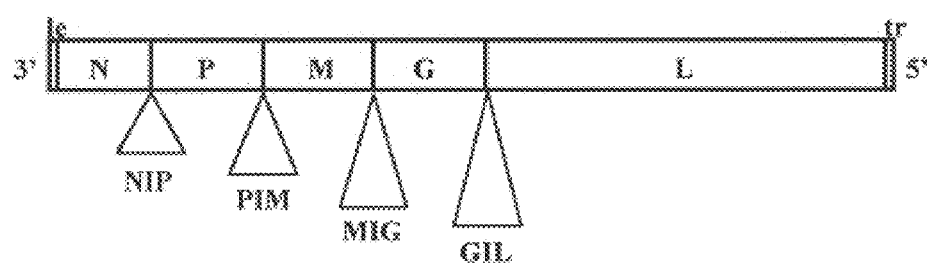

The viruses with the foreign gene sequence inserted at each position in the genome were each used to infect BHK-21 cells and synthesis of RNAs was analyzed by metabolic labeling with [$^3$H]-uridine in the presence of actinomycin D. VSV genomic RNA and the 5 VSV specific mRNAs were expressed from all of the recovered viruses (FIG. 16). In addition, in all four cases, the synthesis of an mRNA of the size expected from the inserted foreign genetic material was also observed. The level of expression of the foreign gene varied as its position of insertion from the 3' end of the genome. The highest level of expression was from NIP, followed by PIM, MIG and GIL (FIG. 16). Thus, these data show that foreign genes may be inserted into the genome of VSV and that the foreign gene will be expressed if surrounded by the conserved VSV gene start and stop signals. Most importantly, this data shows that the level of expression of the foreign gene is controlled by the position at which the gene is inserted into the genome.

Analysis of the growth potential of each of the viruses expressing a foreign gene showed that the position of the insertion of the foreign gene determined whether or not there was an effect on viral growth. NIP was reduced by 10-fold in viral yields compared to wild-type virus, whereas PIM, MIG and GIL all replicated to levels equivalent to that of wild-type virus. Thus, these data show that insertion of a foreign gene is possible, that it is not lethal to the virus, and that it may, depending on the position of insertion, serve to attenuate replication.

Example 21

Viruses and Cells

The San Juan isolate of the Indiana serotype of VSV provided the template for all of the cDNA clone of the VSV genome except the G protein gene which was derived from the Orsay isolate of VSV-Indiana. All viruses were recovered from cDNAs in baby hamster kidney (BHK-21) cells. BHK-21 cells were also used for single-step growth assays and radioisotopic labeling of viral RNAs and proteins. Plaque assays were performed on the African green monkey cell line Vero-76.

Example 22

Plasmid Construction and Recovery of Infectious Virus

The construction of a full-length cDNA clone of the VSV genome and its use for the recovery of infectious virus has been described. This infectious clone was manipulated using methods which allowed the genome to be assembled with the genes in different orders. No other changes were made in the genome except for a single nucleotide in the intergenic region downstream of the P gene. This change, from 3'-CA-5' to 3'-GA-5', has little effect on transcription.

To recover infectious viruses from the rearranged cDNA clones, BHK-21 cells were infected with a recombinant vaccinia virus expressing the T7 RNA polymerase (vTF7-3) (Fuerst, et al., 1986). One hour later the cells were transfected with the rearranged VSV CDNA along with three plasmids, which expressed the N, P, and L proteins required for encapsidation and replication of the anti-genomic RNA (Whelan et al., 1995). Infectious viruses were harvested from the supernatant medium and amplified in BHK-21 cells at low multiplicity of infection (MOI) to avoid formation of DI particles and in the presence of cytosine arabinoside (25 µg/ml) to suppress the replication of vaccinia virus. Supernatant medium was filtered through 0.2 µM filters and the virus was banded on 15 to 45% sucrose velocity gradients to separate it from any remaining vTF7-3 vaccinia virus. The gene orders of the recovered viruses were confirmed by amplifying the rearranged portions of the genomes using reverse transcription and PCR followed by restriction enzyme analysis.

Example 23

Analysis of Viral Protein Synthesis

Viral protein synthesis directed by each of the variant viruses was measured in BHK-21 cells infected at a MOI of 50 with actinomycin D (5 µg/ml) added at 3 hours post-infection. At 5 hours post-infection the cells were washed and incubated in methionine-free medium for 30 min. Cells were exposed to [$^{35}$S]methionine (30 µCi/ml, sp act 10.2 mCi/ml) for 1 hour. Cell monolayers were harvested directly into gel loading buffer and after normalizing for equal counts per minute (cpm) the viral proteins were separated on 10% polyacrylamide gels using a low bis to acrylamide ratio to separate the P and N proteins. Viral proteins were quantitated using a phosphorimager and the molar ratios calculated.

Example 24

Analysis of Virion Proteins

To assess the quantity of each of the proteins in the mature virions, BHK-21 cells were infected at a MOI of 5. After 2 hours the cells were washed and incubated in methionine-free medium for 30 min. Cells were labeled with [$^{35}$S] methionine (50 µCi/ml, sp act 10.2 mCi/ml) overnight with cold methionine added to 10% of normal medium level. Supernatant fluid was collected, cell debris was removed by centrifugation, and virus was collected by centrifugation through 10% sucrose. After normalizing the cpm, the viral pellet was resuspended in gel loading buffer and virion proteins separated on a 10% polyacrylamide gel. Virion proteins were quantitated using a phosphorimager and the molar ratios determined.

Example 25

Single Cycle Virus Replication

BHK-21 cells were infected at a multiplicity of infection (MOI) of 3. After 1-hour adsorption the inoculum was removed and the monolayer washed twice. Fresh medium was added and the cells incubated at 37° C. Supernatant fluids were harvested at indicated intervals over a 30-hour period and viral yields determined by plaque assay on Vero 76 cells.

Example 26

Lethality in Mice

Male Swiss-Webster mice, 3–4 weeks old, were purchased from Taconic Farms German-town, N.Y., and housed under BL2 containment conditions. Groups of 6 mice were lightly anesthetized with ketamine/xylazine and inoculated intranasally with 10 µl aliquots of serial ten-fold viral dilutions of the individual viruses in Dulbecco modified Eagle medium (DMEM). Control animals were given a similar volume of DMEM. Animals were observed and each group was weighed daily. The 50% lethal dose ($LD_{50}$) for each of the viruses was calculated using the method of Reed and Muench (1938).

Example 27

Determination of Serum Antibody Levels and Neutralization Titers

After virus inoculation blood was collected at weekly intervals from groups of 2–4 animals. Serum was pooled and heated to 57° C. for 40 min to inactivate complement. Cell monolayers infected with VSV wild-type (N1G4) and uninfected BHK-21 cells were lysed in detergent buffer (1% NP40, 0.4% sodium deoxycholate, 66 mM EDTA, 10 mM Tris-HCl pH 7.4) and used as antigen in a direct enzyme-linked-immunosorbant-assay (ELISA). Samples were serially diluted and detected using goat α-mouse Ig conjugated to horseradish peroxidase. The optical density (OD) was read at 450 nm and the antibody titers calculated by linear regression analysis of a plot of optical density versus serum dilution. The endpoint titers ($\log_{10}$) were deduced at an OD 1.5 times the pre-immune samples. Serum neutralizing antibody titers on day of challenge were determined by a standard plaque reduction assay on Vero 76 cells and the titer expressed as the reciprocal of the dilution giving 50% neutralization.

Example 28

Protection of Mice From Wild-type Challenge

Mice were immunized intranasally with doses of each virus ranging from 1–10,000 plaque-forming units (pfu) in DMEM. Twenty-one days post-inoculation groups of mice that received non-lethal doses of each of the variant viruses were challenged intranasally with $5.4 \times 10^6$ PFU of N1G4 wild-type virus. Challenged animals and controls were monitored for a further twenty-one days. At weekly intervals blood was collected by tail bleeds for serum antibody titrations.

Example 29

Generation and Recovery of Rearranged Viruses

Figure 17:
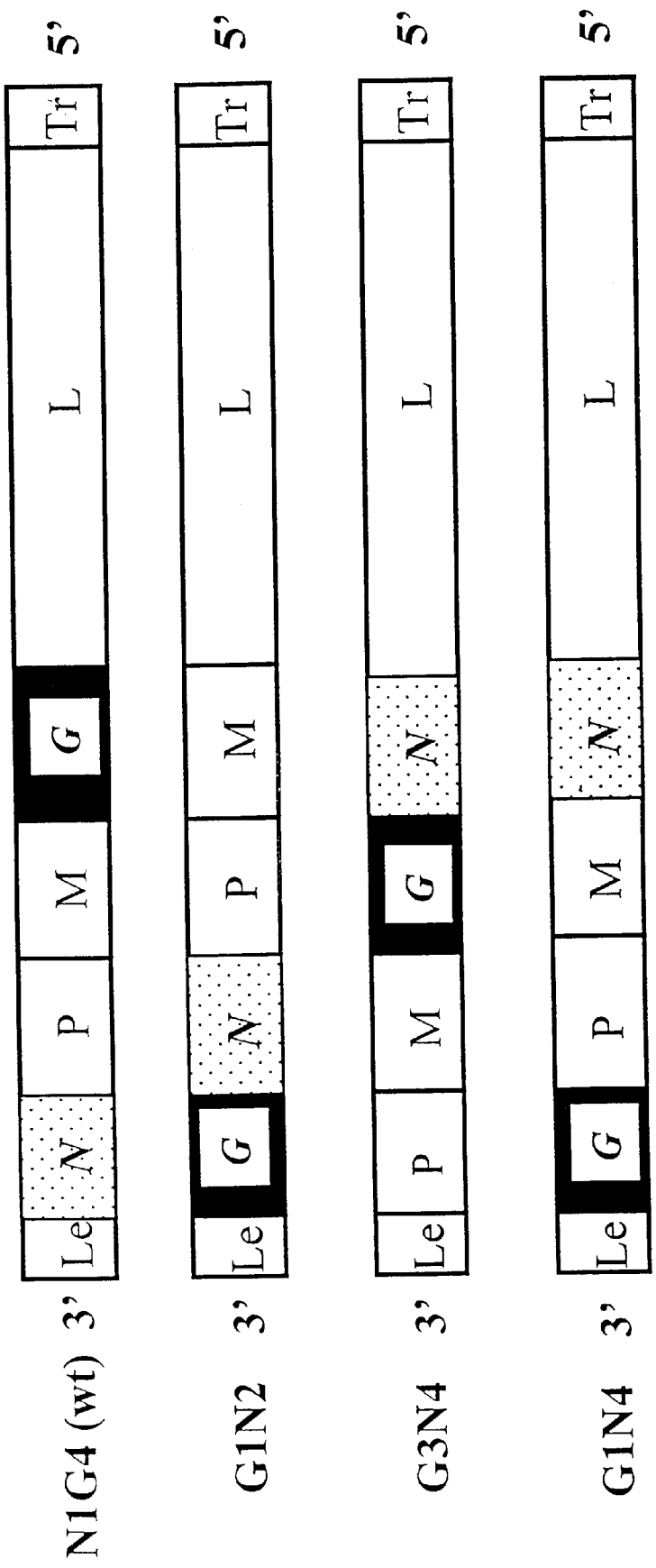
FIG. 17 shows the gene order of the variant viruses: N1G4 (wild type), G1N2, G3N4, and G1N4.

In the present work, cDNA clones were generated in which the G gene was moved from its normal position of fourth in the gene order, to the first, most promoter proximal position to increase its expression. Two new gene rearrangements were generated: one in which the G gene was moved to first in the gene order and the remaining four genes were left undisturbed to generate the order 3'-GNPML-5' (G1N2), and the second in which the positions of the G and the N genes were exchanged to generate the order 3'-GPMNL-5' (G1N4), (FIG. 17). These cDNAs were transfected into cells and virus was recovered in both cases. The recovered viruses were designated G1N2 and G1N4 respectively, according to the positions of the N and G genes in the rearranged gene order. The properties of these viruses were examined in comparison to a virus derived from a cDNA clone created using the same gene rearrangement process to regenerate the wild-type gene order (N1G4), and a virus with the gene order 3'-P-M-G-N-L-5' (G3N4).

Example 30

Effect of Gene Rearrangement on Viral Protein Expression

Figure 18A:
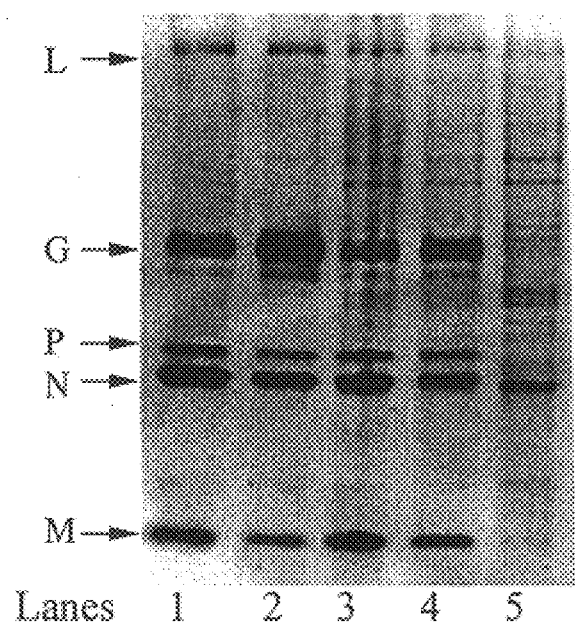
In FIG. 18A, BHK-21 cells were infected at a MOI of 50 and incubated at 37° C. for 5 hr in the presence of actinomycin D (5 μg/ml) for the final 2 hr. Infected cells were then starved for methionine for 30 min and exposed to medium containing [$^{35}$S]methionine (30 μCi/ml) for 1 hr. Total infected cell proteins were analyzed by SDS-PAGE.
Figure 18B:
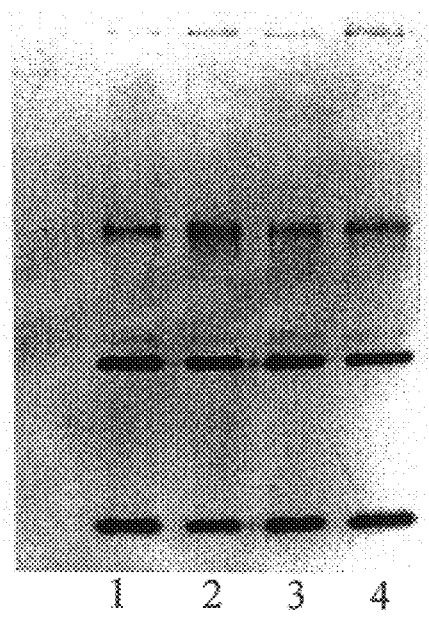
In FIG. 18B, virions were isolated from supernatant fluids of BHK-21 cells infected at a MOI of 5 and exposed to [$^{35}$S]methionine (50 μCi/ml) from 2.5 to 12 hr post-infection. Virus particles were purified by centrifugation through 10% sucrose and their protein contents determined by SDS-PAGE. Viral proteins shown in FIG. 18A and FIG. 18B were quantitated by phosphorimaging and expressed as molar percentages of each viral protein in infected BHK-21 cells in FIG. 18C or molar percentages of each protein in purified virions in FIG. 18D. Data shown average two independent experiments. Lanes: 1, N1G4 (wt); 2, G1N2; 3, G3N4; 4, G1N4; 5, uninfected cells.

BHK-21 cells were infected with viruses with rearranged genomes and the relative levels of viral protein synthesis were examined by labeling for 1 hr with [$^{35}$S]methionine at 5 hr post-infection. Total cellular proteins were resolved by SDS-PAGE and visualized by autoradiography. A typical gel is shown in FIG. 18A. Infection with wild-type VSV and the rearranged variants resulted in rapid inhibition of host protein synthesis which allowed the viral N, P, M, G, and L proteins to be detected directly. Synthesis of G protein was significantly increased relative to the other viral proteins in cells infected with G1N2 and G1N4 viruses (FIGS. 18A and 18B, lanes 2 and 4) as compared to the rate in wild-type (N1G4) infected cells (FIGS. 18A and 18B, lane 1).

Proteins were quantitated by phosphorimaging. The molar percentage of G protein synthesized during a 1 hr labeling period was 2.3-fold higher in G1N2 infected cells and 1.7-fold higher in G1N4 infected cells than in cells infected with wild-type virus. Similarly, translocation of the N gene from its promoter proximal position to a more distal position in viruses G1N2, G3N4, and G1N4 decreased the rate of N protein synthesis (FIG. 18C). As a consequence of these changes in the relative rates of synthesis, the molar ratios of the viral proteins differed in cells infected with the variant viruses, in particular the ratio of N to P which is known to be critical for optimal RNA replication (Pattnaik and Wertz, 1990) (FIG. 18C).

The protein contents of purified virus particles were also examined to determine if changes in protein synthesis in cells affected protein assembly into virions. BHK-21 cells were infected with each of the viruses, labeled with [$^{35}$S] methionine overnight, and virions harvested from supernatant fluids and separated from cell debris by centrifugation through 10% sucrose. Analysis of the virion proteins by SDS-PAGE (FIG. 18B) showed no gross differences in the relative protein contents. Phosphorimager quantitation confirmed that despite the altered relative levels of protein synthesis in infected cells the amounts of proteins in virions were similar to that of wild-type virus, with the exception of virus G1N2 in which the level of G was 1.6-fold higher than in wild-type or the other rearranged viruses (FIG. 18D).

Example 31

Virus Replication in Cell Culture

Figure 19:
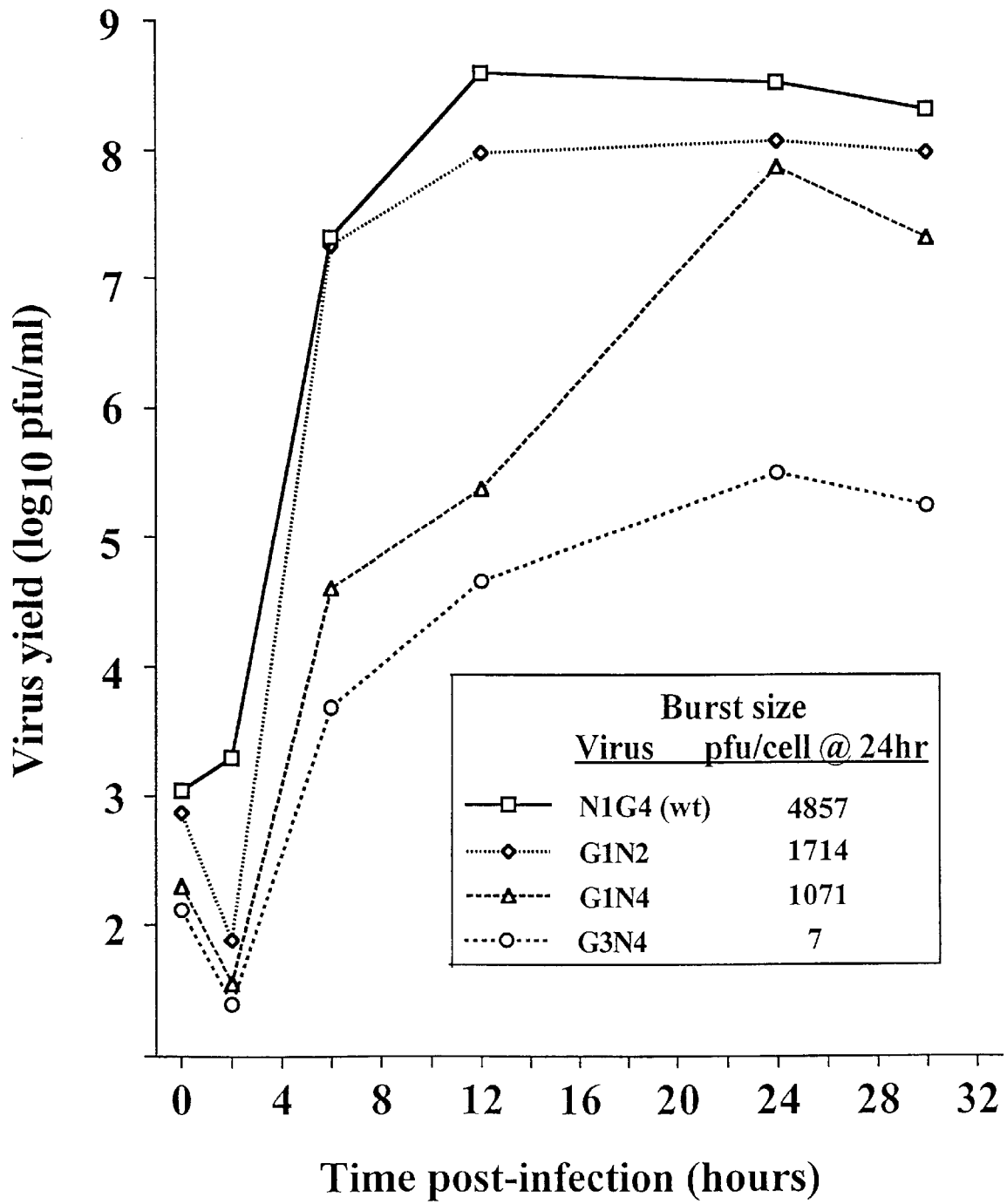
FIG. 19 shows single-step growth analysis. Viruses were assayed for their ability to replicate by single-step growth in BHK-21 cells at 37° C. Cells were infected at a multiplicity of infection of 3 and samples of the supernatant medium harvested at the indicated time points. Samples were titrated in duplicate by plaque assay on Vero-76 cells. Average virus yields per cell were determined at 24 hr post-infection (inset).

Replication of the rearranged viruses under single-step growth conditions was examined in cultured BHK-21 cells infected at a MOI of 3 followed by incubation at 37° C. Supernatant fluids were harvested at various times and the virus yields measured by plaque assay. Translocation of the N gene away from the promoter proximal position resulted in stepwise reduction of replication as the gene was moved further from the first position. Movement of N to the second position (G1N2) decreased replication by 3-fold, whereas moving N to the fourth position (G3N4) reduced replication by as much as 1,000-fold (FIG. 19). However the two viruses with N in the fourth position (G3N4 and G1N4) replicated to very different levels under single-step growth conditions possibly because the molar ratio of N:P critical for optimal replication was less perturbed in G1N4 than G3N4. Measurement of the intracellular rates of protein synthesis 5 hours after infection showed a molar ratio for N:P of 1:1.6 in cells infected with G1N4 (3'-GPMNL-5') compared to a N:P ratio of 1:1.8 in G3N4 (3'-PMGNL-5') infected cells (FIG. 18C). A molar ratio for N:P of between 1:0.5 and 1:1 is optimal for replication as shown by the N:P ratios of 1:0.7 in wild-type-infected cells (N1G4) and 1:0.8 for cells infected with G1N2. Both the wild-type virus and G1N2 have N directly followed by P in the gene order (FIG. 17). Too much or too little P relative to N decreases replication significantly; thus, in cells infected with virus G3N4, not only is N limiting, but also the molar ratio of N:P is more than twice the optimal value. The kinetics of replication of G3N4 and G1N4 were delayed in comparison to wild-type and G1N2. Single-step growth of G3N4 and G1N4 was not complete until 24 hr. post-infection compared to 12 hr for N1G4 and G1N2. It is unlikely that the over abundance of G in the infected cell was responsible for this delay in replication since G1N2 showed no delay in replication relative to wild-type virus.

Example 32

Lethality in Mice

Young mice provide a sensitive animal model for the study of neuropathology caused by VSV and its mutants, (Sabin and Olitsky, 1938; Wagner, 1974) and inoculation of mice with wild-type VSV via the intranasal route results in fatal encephalitis. The pathogenesis of the rearranged variant viruses was compared to that of wild-type virus after intranasal inoculation in 3–4 week old Swiss-Webster mice. The doses that constitute an LD$_{50}$ for each of the viruses are shown in Table 4.

TABLE 4

| LD$_{50}$ dose for mice of viruses with rearranged gene orders | |
|---|---|
| Virus | pfu |
| N1G4 (wt) | 100 |
| G1N2 | 50 |
| G3N4 | >100,000 |
| G1N4 | 19,000 |

*The LD$_{50}$ values were calculated from the observed mortality among groups of 6 mice inoculated intranasally with a series of 10-fold dilutions of the rearranged viruses. Virus titers were determined by plaque assay on Vero-76 cells. Data from a single, internally controlled experiment is shown.

All the viruses were lethal for mice if given in sufficiently high doses, although the doses of G3N4 administered in these experiments did not reach the LD$_{50}$ seen previously. In general the position of the N gene, the N:P ratio, and the resulting level of virus replication were major determinants of lethality. Viruses in which the N gene was moved away from the promoter required greatly increased doses to constitute an LD$_{50}$. These results confirmed previous observations with viruses N1–N4 in which the N gene was moved sequentially. However, the results presented here show that for viruses with N in the fourth position (G3N4 and G1N4), both the replication ability and the LD$_{50}$ values were affected also by the position of the G gene.

The LD$_{50}$ values reported here are expressed in terms of the viral titers on Vero-76 cells which are about 10-fold higher than the titers on BSC-40 cells. Cell lines were changed because rearranging the gene order of VSV could affect the interactions of the variant viruses with the interferon system. BSC-40 cells are competent to produce interferon after infection while Vero cells are not. Therefore changing to Vero cells circumvented possible differences in interferon induction or sensitivity.

Figure 20:
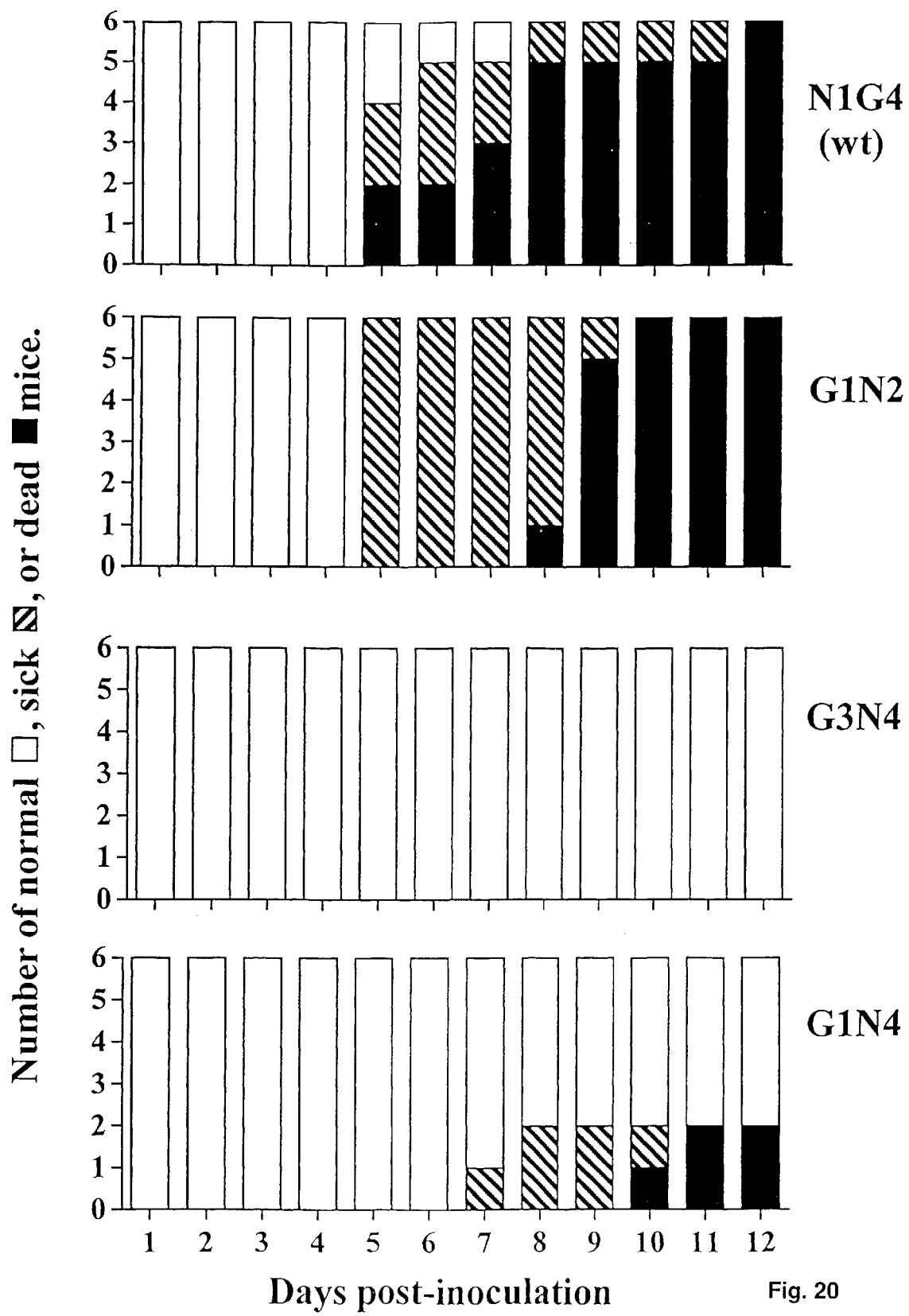
FIG. 20 shows pathogenesis in mice. The viruses shown were administered intranasally to groups of 6 mice at a dose of 1,000 PFU per mouse, and the animals were monitored daily for signs of morbidity and mortality. No further changes occurred after day 12.
Figure 21:
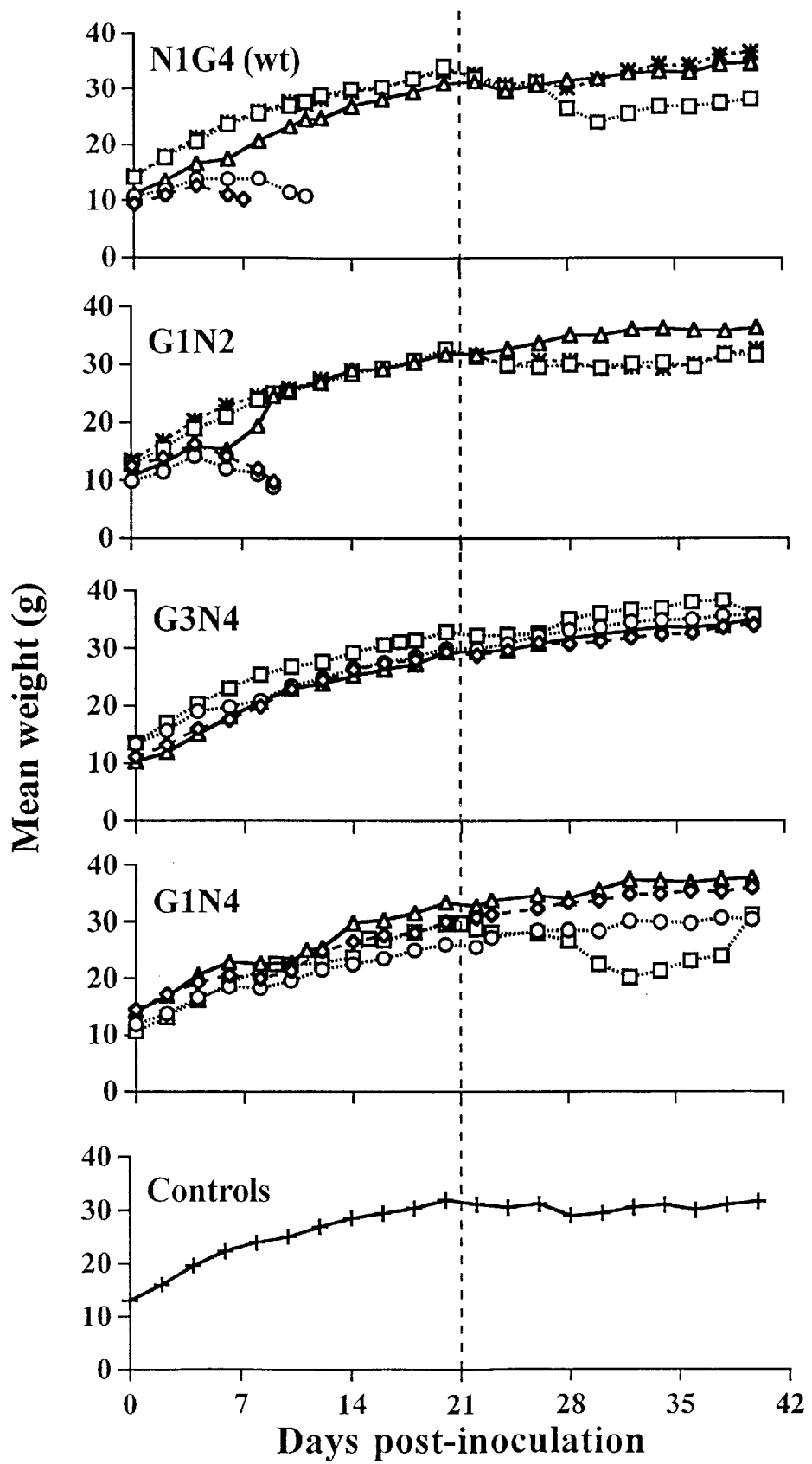
FIG. 21 shows average weight of mice inoculated with the rearranged viruses. Groups of 6 mice were inoculated intranasally with serial 10-fold dilutions of N1G4 (wt), G1N2, G3N4, or G1N4 ranging from 10,000 to 1 pfu/animal. Control mice received inoculation medium alone. The vertical dotted line indicates day of challenge with $5.4 \times 10^6$ pfu/mouse of wild-type virus. For each group, all living animals were weighed together and the average weight determined. ✽, 10,000 pfu; ①, 1,000 pfu; ¬, 100 pfu; o, 10 pfu; †, 1 pfu; +, medium.

The first symptoms of sickness (a hunched posture and hind-limb paralysis) appeared 5 days post-inoculation with both N1G4 and G1N2 viruses although the first deaths occurred earlier in animals inoculated with N1G4 (FIG. 20). The viruses with N in the fourth position induced symptoms more slowly and at a dose of 1,000 PFU per mouse, G3N4 induced neither morbidity nor mortality, as observed before. In an attempt to detect sub-clinical signs of sickness the groups of mice were weighed daily throughout the study period (FIG. 21). However, whereas the mice that showed symptoms invariably lost weight and died, those that showed no symptoms showed no weight differences from uninoculated control animals (FIG. 21). Similar results were observed after challenge of the inoculated mice with wild-type virus: all animals that developed symptoms subsequently died and those that did not develop symptoms also showed no weight loss.

Example 33

Serum Antibody

Figure 22:
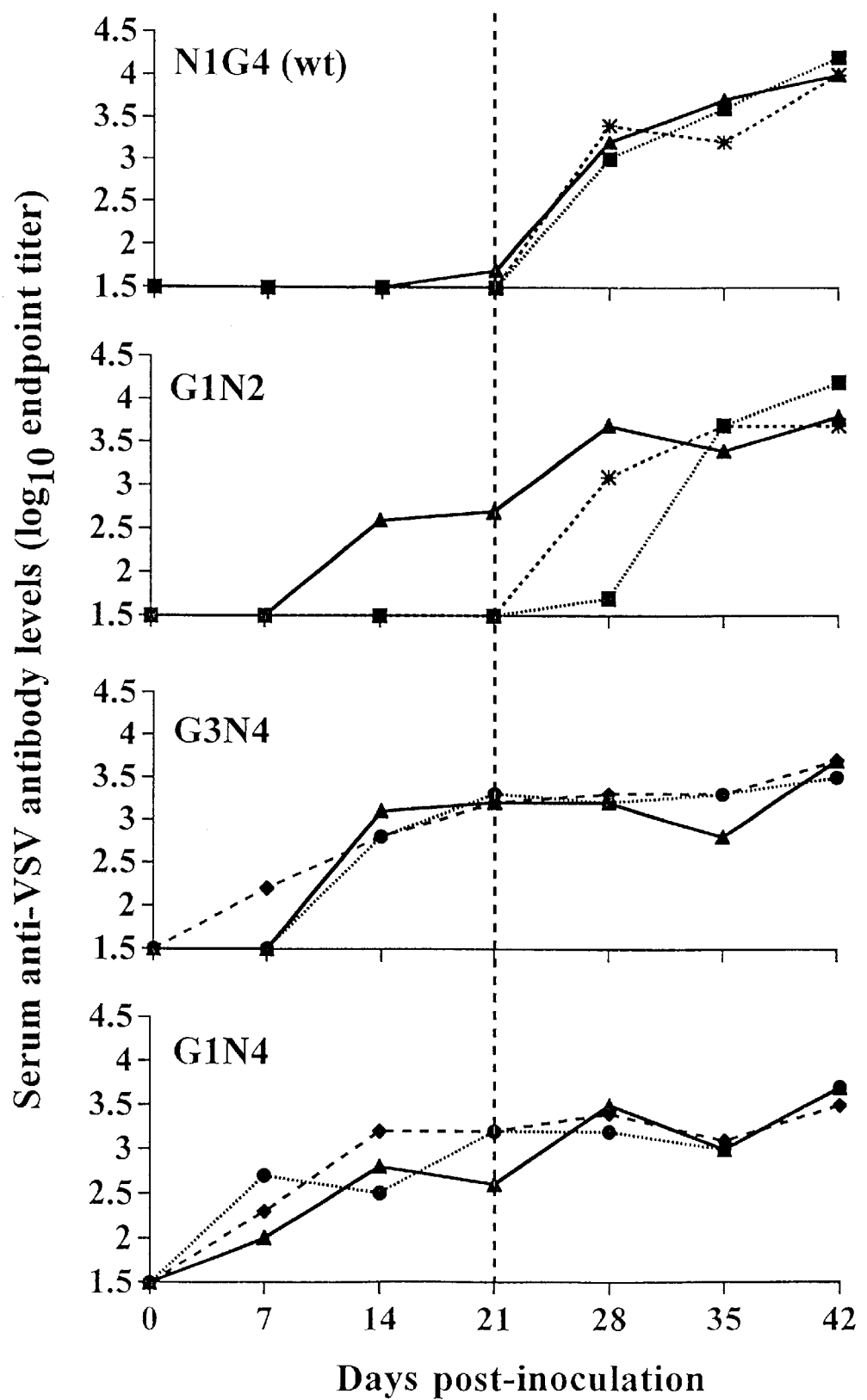
FIG. 22 shows kinetics of antibody production in response to inoculation with the rearranged and wild-type viruses. Groups of 6 mice were inoculated intranasally with serial 10-fold dilutions of N1G4 (wt), G1N2, G3N4, or G1N4 ranging from 10,000 to 1 pfu/animal. Control mice received inoculation medium only. The vertical dotted line indicates the day of challenge with $5.4 \times 10^6$ pfu/mouse of wild type virus. Serum was collected by tail bleeds from 2–4 animals at weekly intervals, the serum pooled and the level of antibody raised against VSV determined by titration on detergent-lysed VSV-infected cell antigen in an ELISA. Antibody levels are expressed as $\log_{10}$ titers. ✽, 10,000 pfu; ①, 1,000 pfu; ¬, 100 pfu; o, 10 pfu; †, 1 pfu; +, medium.

To assess the effect of inoculation of viruses with rearranged G genes on the humoral immune response, mice were inoculated intranasally with a serial 10-fold dilutions of each of the variant viruses. Blood was collected at weekly intervals by tail bleed and the level of serum antibody determined by ELISA. Since survival of the inoculation was a prerequisite for this experiment, only doses at or below the $LD_{50}$ were used. Translocation of the G gene changed the kinetics and magnitude of the antibody response (FIG. 22). Mice inoculated with wild-type virus made barely detectable levels of antibody within 21 days, whereas animals that received 100 PFU of G1N2 had significant titers by 14 days and those given G1N4 had significant titers by 7 days post-inoculation. This accelerated and enhanced response can be seen most clearly by comparing the mice that received 100 PFU (FIG. 22). The results demonstrate that translocation of the G gene from the fourth to the first position enhances the humoral immune response to VSV. Mice given G1N4 synthesized antibody earlier and at higher levels than those given G3N4. This further confirms the observation that putting the G gene first in the gene order increased the immunogenicity of VSV.

Twenty-one days post-inoculation, the mice were challenged with $5.4 \times 10^6$ PFU of wild-type VSV. A rapid increase in antibody titer was observed in animals given either N1G4 or G1N2, although there was no further rise in the already high titers that had been achieved prior to challenge in mice inoculated with G3N4 or G1N4.

Example 34

Neutralizing Antibody Titer After Inoculation

The level of neutralizing antibody in the serum at the time of challenge was measured. In mice and cattle, neutralizing antibodies are an important element in protection against VSV infection. On the day of challenge mice were bled and serum samples were assayed for their ability to neutralize wild-type VSV in a standard plaque-reduction assay on Vero-76 cells. The reciprocal of the highest dilution that gave a 50% reduction of plaque numbers was calculated to determine the neutralizing titers of the sera.

Figure 23A:
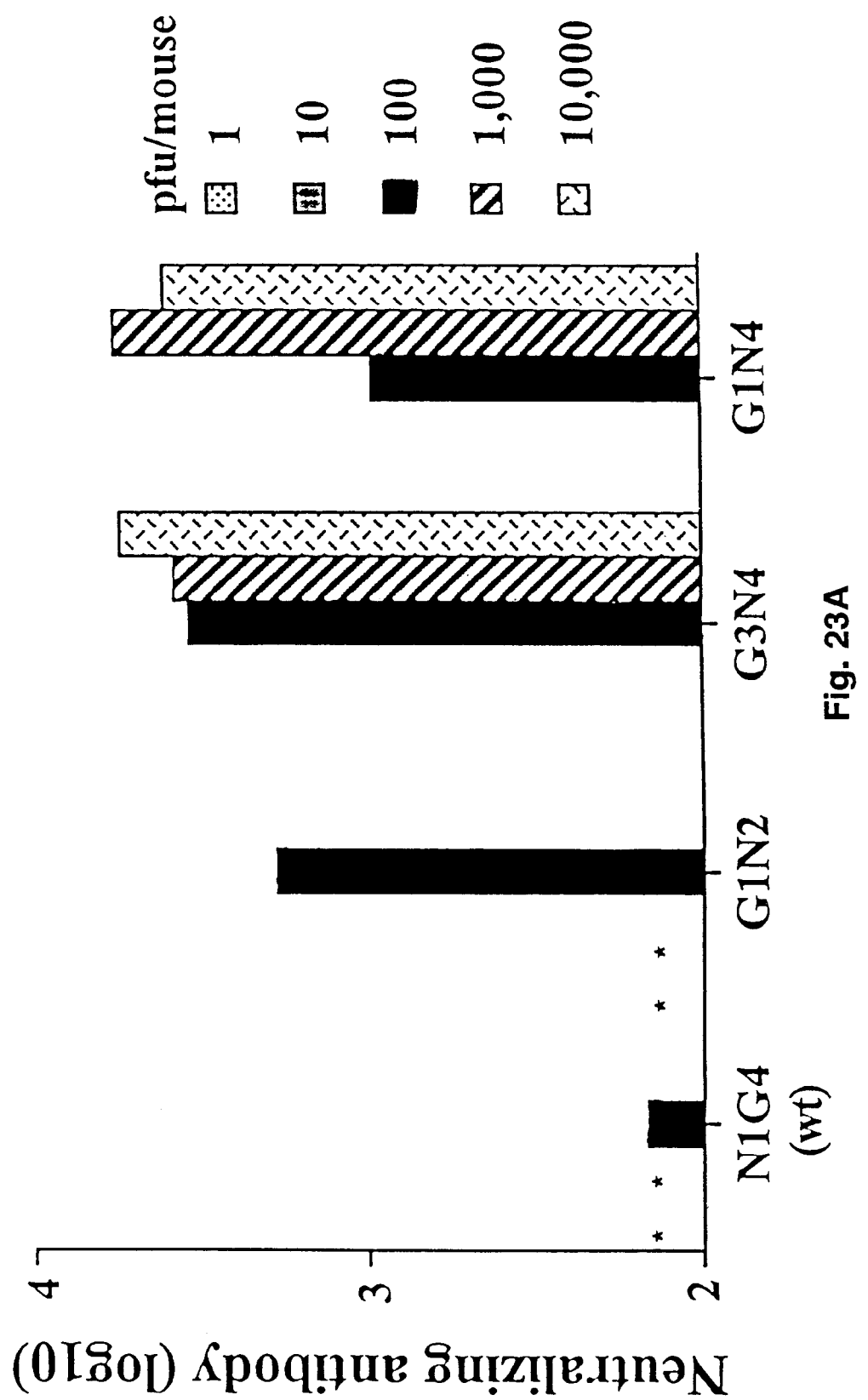
FIG. 23 shows that groups of 6 mice were inoculated intranasally with serial 10-fold dilutions of N1G4 (wt), G1N2, G3N4, or G1N4 ranging from 10,000 to 1 pfu/animal. Control mice received inoculation medium only. Mice were assessed for neutralizing antibody levels as measured in serum samples on the day of challenge by plaque reduction assay (FIG. 23A). Neutralizing antibody levels are expressed as the reciprocal of the highest dilution giving a 50% reduction in wild-type virus plaques on Vero-76 cells. * sera from animals given 1 PFU or 10 PFU of N1G4 or G1N2 virus had background levels of neutralizing antibody. Mice were also assayed for ability to survive intranasal challenge by $5.4 \times 10^6$ PFU of N1G4 virus (FIG. 23B). The dotted line shows the lethality of this dose (83%) in unvaccinated, age-matched, control animals 21 days after challenge.

All the viruses with rearranged genomes elicited serum neutralizing antibody in mice (FIG. 23A). Neutralizing antibody was not detected at doses of 1 or 10 pfu/mouse of either N1G4 or G1N2, but both viruses elicited detectable titers at doses of 100 pfu, the response to G1N2 being 10-fold higher than that to wild-type virus. Thus for N1G4 and G1N2 the level of neutralizing antibody did not correlate with virus replication in cell culture, where the wild-type virus replicated 2–3 fold more abundantly than G1N2 (FIG. 19). This conclusion was reinforced by the response to G3N4 and G1N4, which elicited approximately 10-fold higher titers than the wild-type virus despite greatly reduced replication potential.

In summary, viruses with over-expressed G and under-expressed N in infected cells yielded increased levels of neutralizing antibody compared to wild-type virus (N1G4) following intranasal inoculation. The combination of over-expressing G and under-expressing N combined this enhanced immunogenicity with virus attenuation which allowed the administration of higher doses that elicited correspondingly higher titers of neutralizing antibodies. Moreover, because of the lower lethality of these viruses, 100 times more virus could be administered without detriment, and under these conditions they elicited up to 100-fold more neutralizing antibody than could be attained in response to wild-type virus.

Example 35

Protection of Mice From Challenge

These results establish that non-pathogenic doses of the viruses that over-expressed G protein could elicit significant humoral immune responses in mice. To see whether immunization with the rearranged viruses could confer protection against VSV disease animals that survived inoculated with each of the rearranged viruses were challenged after 21 days with $5.4 \times 10^6$ PFU of wild-type virus. This dose was sufficient to kill 83% of the uninoculated, age-matched, control group of animals.

Figure 23B:
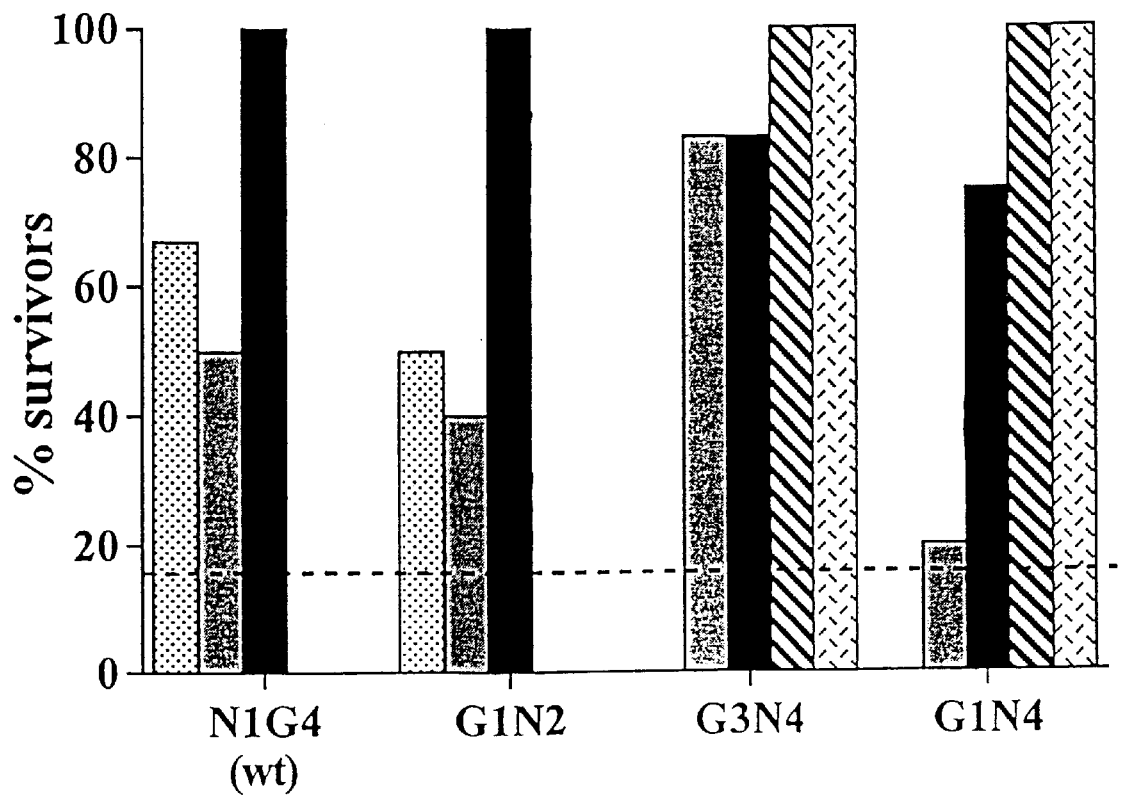

All the viruses with rearranged genomes conferred protection, the level of which varied with the dose of inoculum (FIG. 23B). The levels of protection elicited by N1G4 and G1N2 were alike, reflecting the comparable levels of replication and lethality of these viruses described previously (FIG. 19 and Table 4). Similarly, the protection conferred by G1N4 resembled that of G3N4. By 21 days post-inoculation, both viruses elicited solid immunity at doses of 1,000 PFU per mouse. Importantly, these fully protective doses were 20–100-fold less than the corresponding $LD_{50}$ values. This emphasizes the conclusion that gene rearrangement is an effective method to systematically change the phenotype of VSV to optimize the properties required of a live attenuated vaccine.

Discussion

The present invention demonstrates that the order of genes in negative strand RNA viruses determines the level of gene expression. The gene order can be rearranged and the levels of expression of the rearranged viral genes reflects their position relative to the 3' promoter of transcription. By rearranging a single gene essential for replication, such as the N (nucleocapsid) gene, to successive positions down the viral genome, it is possible to affect the growth potential in cell culture and the lethality of the virus for mice in a stepwise manner. Thus, these data demonstrate a means of attenuating these viruses in a stepwise manner. Attenuated viruses, such as N4 (3'-PMGNL-5'), are such that the lethal dose and the protective dose of the virus differ by over 1000-fold, an attribute desirable for an attenuated vaccine candidate.

In addition, the present invention demonstrates that one may insert foreign genes into the genome of the negative strand virus, and recover infectious virus which expresses the foreign gene. The level of expression of the foreign gene can be controlled by the position in the genome relative to the 3' end at which the gene is inserted. The ability of these viruses to accommodate foreign material is most likely due to the fact that they possess helical ribonucleocapsids, such that the nucleocapsid and the virus both become larger as the size of the genome is increased. No limit on the amount of foreign material that may be inserted has been reached.

The methodology of the present invention can be used to develop attenuated viruses for vaccines, and such methodology is applicable to all members of the family Mononegavirales based upon the close similarity of the genome organization and mechanism for control of gene expression for the members of the family. The Mononegavirales include the Rhabdoviruses, such as rabies, the Paramyxoviruses, such as measles, parainfluenzaviruses, and respiratory syncytial virus, and the Filoviruses such as Ebola and Marburg.

The recovery of infectious viruses from cDNA clones of the Mononegavirales permits experimental manipulation of the viral genome. Gene expression in these viruses is controlled at the transcriptional level by the order of the genes relative to the single promoter at the 3' end of the viral genome. A method to rearrange the order of the genes without introducing other changes into the genome was developed. Gene rearrangement altered the relative levels of synthesis of the viral proteins as expected, and produced infectious viruses having a variety of different phenotypes. The present studies examined the consequences of moving the G protein gene, which encodes the major neutralizing epitopes of the virus, from its promoter-distal position to first in the gene order. Expression of G protein in infected cells was significantly increased when its gene was moved from the fourth to the first position. However, the protein content of the purified virus particles was largely unaffected by changes in the viral gene order.

The over-expression of G protein by these viruses allowed examination of whether they elicited an altered humoral immune response in animals. The data in FIG. 22 show that at an inoculum dose of 100 pfu, antibody was produced more quickly and at higher levels in animals infected with the viruses with G moved to a promoter proximal position as compared to the wild-type virus. Doses higher than 100 PFU could not be assayed for the N1G4 wild-type and G1N2 viruses because of their lethality. When compared at the dose of 100 pfu, viruses G1N2, G3N4, and G1N4 all elicited higher antibody titers more rapidly than wild-type virus. The reduced lethality of the G1N4 and G3N4 viruses allowed higher doses to be administered and in these cases antibody levels increased more rapidly than at lower doses.

The observation that all three viruses which had G move to a promoter proximal position elicited an enhanced humoral immune response in mice has implications for the understanding of protective immunity in this system. Although the relative levels of replication of the variant inocula in the cells that are most relevant for induction of the immune response are unknown, it seems likely that they mirror, at least qualitatively, the relative levels of replication seen in cell culture. If this is the case, G1N2, G3N4, and G1N4 express higher levels of G protein per inoculated mouse only during the first round of replication. After that, the more robust replication of the wild-type virus should have more than compensated for its weaker G protein synthesis. Yet at the same inoculated dose of 100 PFU per mouse, the variant viruses elicited an enhanced and accelerated humoral immune response compared to the wild-type inoculated animals. It is remarkable that a modest increase in the rate of G protein synthesis in infected cells should exert such a marked effect on the immune response, even in the face of substantial attenuation of viral replication.

These results suggest that the kinetics and magnitude of the humoral immune response becomes established very early in infection. Either there is a short temporal window during which the scale of the immune response becomes established irrevocably, or the immune response to VSV infection is somehow determined by the level of G protein synthesis per infected cell rather than by the aggregate immunogenic load. A similar conclusion is suggested by the efficacy of vaccines using recombinant canarypox vectors under conditions where they are unable to replicate. Robust synthesis of antigen by a highly attenuated vector appears to be an effective vaccine strategy that warrants further exploration.

The position of the N gene and the level of N protein expression correlated with efficiency of replication as the N protein is required in stoichiometric amounts for genomic RNA replication. The wild-type virus N1G4 replicated to the highest titers, followed by virus G1N2 and viruses G1N4 and G3N4, which replicated least well. Virus G1N4 however, replicated significantly better than virus G3N4 although they both have the N gene in the fourth position. Both of these viruses showed delayed replication kinetics as might be expected if the formation of progeny virus was limited by the supply of N protein.

It is known that the relative levels of the N and P proteins, in addition to the absolute amount of N protein, are critical for efficient replication. One function of the P protein is to maintain the N protein in a soluble state such that it is able to support encapsidation of newly replicated RNA. Consistent with this, virus G1N2, while having reduced N protein expression (FIGS. 18A and 18C) has the N and P genes in the same relative order as the wild-type virus N1G4 (FIG. 17). Accordingly, G1N2 expressed the N and P proteins at about the same relative rates as wild-type virus, 1:0.8 and 1:0.7 respectively. In agreement with this, virus G1N2 replicated only slightly less than the wild-type virus. Further to this point, although viruses G1N4 and G3N4 both have N in the fourth position, G1N4 replicates substantially better than G3N4 (FIG. 19). The ratio between the rates of synthesis of the N and P proteins is disparate from the wild-type in both of these viruses. However, virus G3N4 which has P in the first position has an N to P ratio in infected cells of 1:1.8 whereas the N:P ratio in cells infected with G1N4, where P is in the second position, is 1:1.6, closer to that of wild-type virus. There is also a difference between these two viruses in the rates of G protein expression and it is possible that the increased levels of Gprotein provide an advantage for replication of virus G1N4.

The reduced lethality of the viruses with gene rearrangements is also consistent with the showing that attenuation of lethality in mice correlated with reduced replication capacity. Reduced replication, in turn, was related to the overall expression levels of N protein and the N to P ratios as discussed above. Obviously any gene rearrangement which brings the G gene to the first position will displace the N gene from its wild-type position and therefore decrease N protein expression. It will also alter the molar ratios of proteins whose gene positions relative to one another are changed by the rearrangement in question. Both types of change would be expected to alter replication efficiency and lethality. The data in Table 4 show that the viruses which replicate best, wild-type and G1N2, required only 50 to 100 PFU to constitute an $LD_{50}$ dose, whereas 200 to 1,000 times more G1N4 and G3N4 virus, respectively, were required for a lethal dose.

The data presented here show that rearrangement of genes allowed the manipulation of two important aspects of the viral phenotype: lethality and the stimulation of neutralizing antibody. By reducing N protein expression, and altering the N:P ratio, it was possible to decrease replication potential and lethality for animals; by increasing G protein expression it was possible to alter the kinetics and level of antibody synthesis.

These results demonstrate that gene rearrangement can be used to generate viruses with novel, beneficial phenotypes. This approach provides the ability to alter the phenotype in a stepwise manner to achieve a desired level of attenuation or to alter the expression of a particular gene. It allows the level of attenuation and immunogenicity to be modulated independently and systematically, exactly what is needed to generate and manipulate live attenuated vaccine candidates. This approach should be applicable to other members of the Mononegavirales, all of which have a common mechanism for the control of gene expression via obligatorily sequential transcription originating from a single 3' promoter. Furthermore, viruses of the Mononegavirales have not been found to undergo homologous recombination, therefore changes made to the gene order should be irreversible by natural processes. Several foreign genes have been expressed from VSV and in one study mice were protected against the corresponding pathogen. These properties of VSV make it an excellent candidate in which to generate future vaccines directed against VSV itself or against other pathogens. Studies designed to evaluate the pathogenesis and immunogenicity of the G1N2, G3N4, and G1N4 viruses in a natural host are underway.

The following references were cited herein:
Ball, L. A. 1992. *J. Virol.* 66, 2335–2345.
Ball, L. and C. White. 1976. *Proc. Natl. Acad. Sci.* USA 73, 442–446.
Barr, J. N. et al., 1997. *J. Virol.* 71, 1797–1801.
Domingo, E. et al., 1996. *The FASEB Journal* 10, 859–864.
Ferran, M. and J. M. Lucas-Lenard. 1997. *J. Virol.* 71, 371–377.
Fuerst, T. et al., 1986. *Proc. Natl. Acad. Sci.* USA 83, 8122–8126.
Iverson, L. and J. Rose. 1981. *Cell* 23, 477–484.
Lyles, D. S. et al., 1996. *Virology* 217, 76–87.
Pattnaik, A. K. and G. W. Wertz. 1990. *J. Virol.* 64, 2948–2957.
Pattnaik, A. K. et al., 1992. *Cell* 69, 1011–1020.
Patton, J. P. et al., 1984. *J. Virol.* 49, 303–309.
Peluso, R. W., and S. A. Moyer. 1988. *Virology* 162, 369–376.
Pringle, C. R. et al., 1981. *J. Virol.* 39, 377–389.
Pringle. C. R., and A. J. Easton, 1997. *Semin. Virol.* 8, 49–57.
Reed, E. J. and H. Muench. 1938. *Am. J. Hyg.* 27, 493–497.
Sabin, A. and P. Olitsky. 1938. *J. Exp. Med.* 67, 201–227.
Schnell, M. J. et al., 1996. *J. Virol.* 70, 2318–2323.
Shechmeister, et al., 1967. *Arch. Ges. Virusforsch.* 21, 127–132.
Villareal, L. P. et al., 1976. *Biochem.* 15, 1663.
Wagner, R. 1974. *Infection and Immunity* 10, 309–315.
Wagner, R. 1996. In Fields *Virology* (Fields, B. N. and D. M. Knipe eds.) $3^{rd}$ edition; Lippincott-Raven Press.
Whelan, S. P. J. et al., 1995. *Proc. Natl. Acad. Sci.* USA 92, 8388–8392.
Wimmer, E. et al., 1993. *Ann. Rev. Genetics.* 27, 353–436.
Youngner, J. S. and G. Wertz. 1968. *J. Virol.* 2, 1360–1361.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and/or specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of attenuating a virus of the order Mononegavirales, comprising the step of:
   rearranging the gene order of said virus by moving a gene away from its wild-type position, wherein said gene is not the nucleocapsid gene of said viris.

2. A method of attenuating a virus of the order Mononegavirales, comprising the step of:
   rearranging gene order of said virus by moving said virus' nucleocapsid (N) gene away from its wild-type 3' promoter proximal position and placing said N gene in the second or third position of said gene order.

3. A virus attenuated according to the method of claim 2.

* * * * *

SEQUENCE LISTING

<160> NUMBER OF SEQ ID NOS: 12

<210> SEQ ID NO 1
<211> LENGTH: 38
<212> TYPE: DNA
<213> ORGANISM: Artificial sequence
<220> FEATURE:
<223> OTHER INFORMATION: PCR primer used to construct individual cDNA
      clones of VSV genes

<400> SEQUENCE: 1
acctgcacta acagaaaaaa actaacagag atgcaggt                                38

<210> SEQ ID NO 2
<211> LENGTH: 23
<212> TYPE: DNA
<213> ORGANISM: Artificial sequence
<220> FEATURE:
<223> OTHER INFORMATION: starting plasmid to reconstruct the rearranged
      full-length clones of N gene, containing a
      bacteriophage T7 promoter followed by the VSV -continued

```
      leader sequence

<400> SEQUENCE: 2
gaaactttaa cagtaatgca ggt                                              23

<210> SEQ ID NO 3
<211> LENGTH: 22
<212> TYPE: DNA
<213> ORGANISM: Artificial sequence
<220> FEATURE:
<223> OTHER INFORMATION: starting plasmid to reconstruct the rearranged
      full-length clones of L gene, containing the
      first 420 nucleotides of the L gene

<400> SEQUENCE: 3
acctgcacta acagcaatca tg                                               22

<210> SEQ ID NO 4
<211> LENGTH: 14
<212> TYPE: DNA
<213> ORGANISM: Artificial sequence
<220> FEATURE:
<221> NAME/KEY: primer_bind
<222> LOCATION: 1, 2, 3, 4, 5, 6, 7,8
<223> OTHER INFORMATION: n = a or g or c or t

<400> SEQUENCE: 4
nnnnnnnngc aggt                                                        14

<210> SEQ ID NO 5
<211> LENGTH: 11
<212> TYPE: DNA
<213> ORGANISM: Artificial sequence
<220> FEATURE:
<221> NAME/KEY: primer_bind
<222> LOCATION: 1, 2, 3, 4, 5
<223> OTHER INFORMATION: n = a or g or c or t

<400> SEQUENCE: 5
nnnnngagac c                                                           11

<210> SEQ ID NO 6
<211> LENGTH: 30
<212> TYPE: DNA
<213> ORGANISM: Artificial sequence
<220> FEATURE:
<221> NAME/KEY: primer_bind
<222> LOCATION: 24, 25, 28, 29, 30
<223> OTHER INFORMATION: n = a or g or c or t

<400> SEQUENCE: 6
gggaagctta cctgcactaa cagnnatnnn                                       30

<210> SEQ ID NO 7
<211> LENGTH: 25
<212> TYPE: DNA
<213> ORGANISM: Artificial sequence
<220> FEATURE:
<221> NAME/KEY: primer_bind
<222> LOCATION: 19, 20, 23, 24, 25
<223> OTHER INFORMATION: n = a or g or c or t

<400> SEQUENCE: 7
tatgaaaaaa actaacagnn atnnn                                            25

<210> SEQ ID NO 8
<211> LENGTH: 34
```

```
<212> TYPE: DNA
<213> ORGANISM: Artificial sequence
<220> FEATURE:
<221> NAME/KEY: primer_bind
<222> LOCATION: 16, 17
<223> OTHER INFORMATION: n = a or g or c or t

<400> SEQUENCE: 8 cttttttga ttgtcnntac gtccagggcc cacg                    34

<210> SEQ ID NO 9
<211> LENGTH: 34
<212> TYPE: DNA
<213> ORGANISM: Artificial sequence
<220> FEATURE:
<221> NAME/KEY: primer_bind
<223> OTHER INFORMATION:

<400> SEQUENCE: 9
gcacccggga cctgcatatc tgttactttt tttc                   34

<210> SEQ ID NO 10
<211> LENGTH: 34
<212> TYPE: DNA
<213> ORGANISM: Artificial sequence
<220> FEATURE:
<221> NAME/KEY: primer_bind
<223> OTHER INFORMATION:

<400> SEQUENCE: 10
gcacccggga cctgcatctc tgttagtttt tttc                   34

<210> SEQ ID NO 11
<211> LENGTH: 34
<212> TYPE: DNA
<213> ORGANISM: Artificial sequence
<220> FEATURE:
<221> NAME/KEY: primer_bind
<223> OTHER INFORMATION:

<400> SEQUENCE: 11
gcacccggga cctgcattgc tgttagtttt tttc                   34

<210> SEQ ID NO 12
<211> LENGTH: 34
<212> TYPE: DNA
<213> ORGANISM: Artificial sequence
<220> FEATURE:
<221> NAME/KEY: primer_bind
<223> OTHER INFORMATION:

<400> SEQUENCE: 12
gcacccggga cctgcatatc tgttagtttt tttc                   34
```